(12) United States Patent
Thorne, Jr. et al.

(10) Patent No.: US 6,254,575 B1
(45) Date of Patent: Jul. 3, 2001

(54) REACCESSIBLE MEDICAL NEEDLE SAFETY DEVICES AND METHODS

(75) Inventors: Gale H. Thorne, Jr., Bountiful; Mark Nelson, Sandy; F. Mark Ferguson, Salt Lake City; Kendall P. Thorne, Kaysville; Michael L. Thorne, Bountiful; David L. Thorne, Kaysville; Gale H. Thorne, Bountiful; Michael A. Wilson, Salem, all of UT (US)

(73) Assignee: Specialized Health Products, Bountiful, UT (US)

( * ) Notice: Subject to any disclaimer, the term of this patent is extended or adjusted under 35 U.S.C. 154(b) by 0 days.

(21) Appl. No.: 09/434,036

(22) Filed: Nov. 4, 1999

(51) Int. Cl.[7] ..................................... A61M 5/32
(52) U.S. Cl. ........................................ 604/198; 128/919
(58) Field of Search .................... 604/198, 192, 604/196, 197, 110, 263, 240, 273, 243, 256, 164.08; 128/912, 919

(56) References Cited

U.S. PATENT DOCUMENTS

| Re. 34,045 | 8/1992 | McFarland . |
|---|---|---|
| 3,587,575 | 6/1971 | Lichtenstein . |
| 4,040,419 | 8/1977 | Goldman . |
| 4,106,621 | 8/1978 | Sorenson . |
| 4,270,536 | 6/1981 | Lemelson . |
| 4,772,272 | 9/1988 | McFarland . |
| 4,790,828 | 12/1988 | Dombrowski . |
| 4,795,432 | 1/1989 | Karczmer . |
| 4,840,619 | 6/1989 | Hughes . |
| 4,846,811 | 7/1989 | Vanderhoof . |
| 4,874,382 | 10/1989 | Lindemann . |
| 4,874,384 | 10/1989 | Nunez . |
| 4,911,694 | 3/1990 | Dolan . |
| 4,929,241 | 5/1990 | Knlli . |
| 4,935,012 | 6/1990 | Magre ................................. 604/192 |

(List continued on next page.)

FOREIGN PATENT DOCUMENTS

| 0 654 281 A2 | 5/1995 | (EP) . |
|---|---|---|
| 0 705 613 A2 | 4/1996 | (EP) . |
| 0 457 477 B1 | 1/1998 | (EP) . |
| 0 815 888 A2 | 1/1998 | (EP) . |
| 0 815 890 A2 | 1/1998 | (EP) . |
| 0 819 441 A1 | 1/1998 | (EP) . |
| 0 553 308 B1 | 2/1998 | (EP) . |
| 0 585 391 B1 | 2/1998 | (EP) . |
| 0 485 345 B1 | 3/1998 | (EP) . |
| 0 832 659 A2 | 4/1998 | (EP) . |
| 0 832 660 A2 | 4/1998 | (EP) . |
| 0 626 924 B1 | 5/1998 | (EP) . |
| 0 603 365 B1 | 9/1998 | (EP) . |
| 0 597 857 B1 | 10/1998 | (EP) . |
| 10076007A | 3/1998 | (JP) . |

(List continued on next page.)

*Primary Examiner*—Anhtuan T. Nguyen
(74) *Attorney, Agent, or Firm*—Paul S. Evans; Gale H. Thorne

(57) ABSTRACT

A retractable and extendable medical needle protective shield which provides opportunity for accessing and reaccessing a medical needle and associated sharpened needle tip and recovering the needle and tip for safety between accesses. The shield includes a needle guide which assures the needle tip is untouched by any part of the shield as the shield is displaced to cover and uncover the needle. A releasible latch is provided to guard against inadvertent removal of the protective shield between accesses. An unreleasible latch is also provided to secure the shield relative to the latch preparatory to final disposal. In combination with the protective shield, a plurality of adapters are disclosed which provide examples of passively operated, protected access to membrane pierceable fluid sources such as a "Y" connection site of an IV set line, a drug vial, a vacuum sample tube, an umbilical cord holder and a hypodermic site.

33 Claims, 35 Drawing Sheets

U.S. PATENT DOCUMENTS

| | | | |
|---|---|---|---|
| 4,935,013 | 6/1990 | Haber . | |
| 4,936,830 | 6/1990 | Verlier . | |
| 4,985,021 | 1/1991 | Straw . | |
| 5,000,744 | 3/1991 | Hoffman . | |
| 5,057,089 | 10/1991 | Greco . | |
| 5,139,489 | 8/1992 | Hollister . | |
| 5,147,303 | 9/1992 | Martin . | |
| 5,154,285 | 10/1992 | Hollister . | |
| 5,176,656 | 1/1993 | Bayless . | |
| 5,195,983 | 3/1993 | Boese . | |
| 5,232,455 | 8/1993 | Hollister . | |
| 5,246,427 | 9/1993 | Sturman . | |
| 5,246,428 | 9/1993 | Falknor . | |
| 5,256,153 | 10/1993 | Hake . | |
| 5,290,255 | 3/1994 | Vallelunga . | |
| 5,304,137 | 4/1994 | Fluke . | |
| 5,348,544 | 9/1994 | Sweeney | 604/192 |
| 5,356,392 | 10/1994 | Firth . | |
| 5,403,286 | 4/1995 | Lockwood . | |
| 5,447,501 | 9/1995 | Karlsson . | |
| 5,466,223 | 11/1995 | Bressler . | |
| 5,487,733 | 1/1996 | Caizza . | |
| 5,498,243 | 3/1996 | Vallelunga . | |
| 5,533,980 | 7/1996 | Sweeney . | |
| 5,643,220 | 7/1997 | Cosme . | |
| 5,695,474 | 12/1997 | Daugherty . | |
| 5,738,665 | 4/1998 | Caizza | 604/263 |
| 5,746,726 | 5/1998 | Sweeney | 604/263 |
| 5,814,018 | 9/1998 | Elson | 604/110 |
| 5,823,997 | 10/1998 | Thorne | 604/110 |
| 5,843,041 | 12/1998 | Hake | 604/198 |
| 5,925,020 | 7/1999 | Nestell | 604/198 |

FOREIGN PATENT DOCUMENTS

| | | |
|---|---|---|
| 10127765A | 5/1998 | (JP) . |
| WO 98/07463 | 2/1998 | (WO) . |
| WO 98/10816 | 3/1998 | (WO) . |
| WO 98/11928 | 3/1998 | (WO) . |
| WO 98/13081 | 4/1998 | (WO) . |

REACCESSIBLE MEDICAL NEEDLE SAFETY DEVICES AND METHODS

FIELD OF INVENTION

This invention relates generally to safety devices for hollow bore medical needles and particularly to syringe needle devices which employ protective needle shields or sheaths for securely shielding sharp needle tips, both before and after being used in a medical procedure. This invention more particularly relates to medical needle shields, sheaths or shrouds which may be used as a removable and replaceable protective needle cover. This invention also relates to connectors or adapters which may be used to further shield and protect a needle during use and which may be keyed for selective release of an associated medical needle shield from a needle tip end of a device.

PRIOR ART

Problems associated with inadvertent needle sticks are well known in the art of blood sampling, percutaneous medication injection and other medical procedures involving uses of medical needles. Ever increasing attention is being paid to needle stick problems due to the contemporary sensitivity of exposure to AIDS, Hepatitis and other serious blood-borne diseases.

Commonly, procedures involving removing a needle from a patient require a technician to use one hand to place pressure at the wound site where the needle is being withdrawn while removing the needle apparatus with the other hand. It is common practice for a tending technician to give higher priority to care for the wound than is given to disposal of a needle. In the case of commonly used, non-safety devices such priority either requires convenience of an available sharps container within ready reach or another means for safe disposal without leaving the patient's side. Providing adequate care, with accompanying safety procedures, is often compounded by patient physical condition and mental state (e.g. in burn units and psychiatric wards). Under such conditions, it is often difficult, if not impossible, to take appropriate procedures to properly dispose of a used, exposed needle while caring for a patient. Further, common practice of filling syringes with medication in one area and then transporting an uncapped needle (recapping a needle is currently discouraged in U.S. medical practice due to dangers associated with recapping) to a patient area provides a significant opportunity for accidental needle sticks.

Widespread knowledge and history associated with needle care and disposal problems have resulted in conception and disclosure of a large number of devices each of which represents an attempt to provide not only a solution to the problem of needle sticks, but also a device which is commercially viable (i.e. cost and price competitive with currently used non-safety devices). In the case of syringes, current devices which are used to shield syringe needles often require two hands and, in some devices, safety status of needle shields are not readily apparent.

Examples of disclosures of safety devices which protect needles by moving a protective shield over a sharp end of a syringe or other hollow bore medical needle are found in U.S. Pat. No. 5,823,997 issued Nov. 17, 1998 to David L. Thorne (Thorne), U.S. Pat. No. 5,348,544, issued Sep. 20, 1994 to Sweeney et al. (Sweeney), U.S. Pat. No. 5,246,428 issued Sep. 21, 1993 to Donald W. Falknor (Falknor), U.S. Pat. No. 5,256,153 issued Oct. 26, 1993 to Lawrence W. Hake (Hake) and U.S. Pat. Nos. 5,139,489 and 5,154,285, issued Aug. 18, 1992 and Oct. 13, 1992, respectively, to William H. Hollister (Hollister). There are many other examples of safety devices which retract needles into housings, however, this instant invention is more directly related to devices which extend a shield over a needle rather than to those which employ needle retraction.

Thorne discloses a safety needle enclosure which is disposed to rotate longitudinally about a needle and, upon being displaced to a needle shielding state, forms a substantially rigid part in cooperation with the needle to thereby provide a safety needle shield. The enclosure comprises a plurality of rigid segments, serially interconnected by a plurality of intersegment hinges, which are preferably living hinges. The segments are disposed about a medical needle, folded upon each other during the medical procedure and extended, only at the end of the procedure, to form a secure, substantially rigid, single-use safety shroud. During the procedure, the enclosure is folded and conveniently disposed about a proximal portion of the needle. At the end of the procedure, the enclosure is extended to protectively sheath and secure the needle in a substantially rigid structure formed by the combination of the enclosure and the needle.

Sweeney discloses a device comprising a guard which is manually, slidably movable along a needle cannula from a site proximal to a user to a distal site where the needle tip is shielded. The device comprises a hinged arm which extends along the needle cannula and which is moved distally to collapse upon itself to extend the shield over the tip. Access to the tip is denied by a metallic clip. An alternative embodiment is also disclosed by which the manual operation is augmented by a spring. A device based upon Sweeney is currently being distributed by Becton Dickinson and Company, Franklin Lakes, N.J. in which three separate parts (two injection molded and one metal clip) are used to mechanize the guard. Once the device is extended to shield a needle tip, it should not be reset to recover use of the needle for a subsequent procedure, and is therefore, like the device taught by Thorne, a single-use device. Also, the hinged arm requires activation in the region of the needle itself and comprises parts which are of a size which occasionally impedes a user's line of sight to insertion locations.

Falkner, and related disclosures, disclose devices comprising shields which are automatically releasible to extend distally from a user to cover a needle. The devices comprise latch mechanisms which are manually switched between unlatched and latched positions to free the needle for use and lock the shield over the needle, respectively. Of course, position of the latch mechanism provides a visual interpretation of the safety of the device (i.e. whether or not a latch is engaged), but that is the only safety mechanism and a "missed" indicator of latch mechanism position may be possible in stressful circumstances. When the latch mechanism is in the unlatched position, access to the needle is not only possible, but likely when the front of the device is impacted by a body part. In addition, the shield, though made of transparent material, covers a portion of an attached syringe body until fully extended and may make accurately reading portions of volume measurement indicia on the syringe body difficult when the syringe is being used in a titrating application.

Hake is representative of disclosure of devices comprising a manually slidable guard which is disposed over a syringe body during a medical procedure involving a medical syringe needle and manually, slidably moved distally into a needle guarding position usually at the end of the procedure. Commonly users of such devices complain of difficulty of seeing measurement indicia while the guard is disposed over the syringe body and of danger of inadvertent needle sticks while sliding the guard distally to cover the needle. As well, it is generally difficult to determine whether a guard is in a locked or unlocked state when it covers the needle, providing an additional possibility of inadvertent needle sticks.

Hollister discloses a needle protection device which may be used with a double-ended needle assembly or with a simpler single needle system. The protection device comprises a substantially rigid housing flexibly connected to a container (for a vacuum tube sampling system) or to a needle hub. To exercise the protection device, the rigid member is pivotally rotated into engagement with an exposed needle of the double-ended needle assembly and is securely affixed to the exposed needle. A major drawback of the needle protection device of Hollister is the size and position of the rigid housing. During use of an assembly or system in a medical procedure, length and position of the housing member is considered by some to be inconvenient. A second drawback is the requirement either for two handed operation to pivot the housing to engage the needle or for the requirement to find and use a stable support surface against which the housing is pressed while the needle is swung into engagement with the housing. In a currently marketed format, an integral container holder version of the device disclosed by Hollister comprises two injection molded parts which permit the housing to be rotated, as much as possible, out of the way during a medical procedure. Such a format requires five injection molded parts, including a disposable needle assembly.

An often occurring circumstance, especially in the use of syringe needles, involves a need to use a needle a plurality of times. As an example, when an intramuscular injection is made, it is common practice to draw contents from a drug vial into a syringe and then inject the contents into a patient. It is desirable to use the same needle for penetrating a membrane on the drug vial and then for injecting the patient. However, the site where contents are drawn from the drug vial may be some distance from a site where the patient is to be injected. Such situations may result in a technician's recapping the needle (a procedure which is currently discouraged and against standard precautions) for transport to the patient. Equally as concerning is another practice of carrying the needle unprotected. Some currently available safety devices, such as those based upon Hake, permit covering and reaccessing a needle; however, other factors, such as those disclosed above have limited acceptance of these safety devices.

Acknowledgment of need for safety, even in situations where a needle is entering a relatively sterile or at least relatively clean field (such as through a "Y" connection in an IV set), has resulted in successful design and marketing of a class of medical devices commonly known as "needleless systems". However, even these systems do not totally eliminate the use of needles, as the procedure for filling a vial (discussed as an example above) still requires use of a sharp needle to fill a syringe. Once the syringe has been filled, it is common practice for the used needle to be removed and discarded and replaced with a blunt cannula or connected to a needleless connector, a seemingly wasteful exercise, and the needle is still exposed and dangerous during the syringe filling procedure.

Generally, other than acceptance of the type of operation offered by such devices, commercial viability is dependent upon manufacturing cost. Purchase decisions in the area in which these devices are used are very cost sensitive. If gains in either improvement in safety or in labor savings are not found to make a device sufficiently competitive with contemporary items currently on the market, those devices are usually not found to be commercially viable.

BRIEF SUMMARY AND OBJECTS OF THE INVENTION

In brief summary, the novel invention disclosed herein dramatically diminishes known major problems resulting from injury-related needle sticks which occur when needle tips are bared as medical needles are withdrawn from a patient at the end of a needle insertion procedure, but, perhaps more important to general patient welfare, these inventions provide opportunity for fabrication of a very low cost safety needle system which permits safety access to a medical needle in several steps in a medical procedure, while being able to return the needle to the safety of a covering enclosure between the steps. Consistent with such uses, the medical needle may be accessed, covered and reaccessed repeatedly for such purposes as protecting a sharpened needle tip in transit before use, ad interim after a preliminary use, such as filling a syringe with a medication, and being displaced to a safety, needle-covering position after a medical procedure is completed.

Basic to the invention is a medical needle device which employs a protective needle shield which may be somewhat similar in form and function to a sheath disclosed in Thorne, but is discernably different in that the shield of the present invention is displaceable to cover and protect a needle tip and which is further displaceable to bare the needle and tip a plurality of times, after being covered, for use throughout a medical procedure.

For reference, Thorne discloses a foldable needle sheath which is articulated to fold about a medical needle to permit access to the needle in a medical procedure. The sheath is hingeably attached to a structure (e.g. a needle hub or phlebotomy barrel) at a point away from a sharpened needle tip which is later enclosed to protect a user. At the end of the procedure, the sheath is unfolded and extended away from the structure in the direction of the needle tip to encase and thereby protect users from contact with the needle and its tip. To permit the sheath to unfold about the needle, each folded part of the sheath is serially constructed of a plurality of rigid and interconnected segments. At least one segment comprises an orifice through which the needle passes and about which each at least one segment rotates while the sheath is being extended. Each segment is connected to at least one other segment by a hinge, which is preferably a molded, living hinge, and comprises a channel into which the needle is nested when the sheath is fully extended. The sheath comprises a catch which securely affixes the sheath when the needle is captured and disposed in the sheath. Once the sheath is extended and the needle so captured, the combination of sheath and needle form a substantially rigid member which shrouds the needle and its sharpened tip to provide safety from dangerous contact with the tip and needle. All hingeable attachments are preferably living hinges integrally and concurrently formed with other sheath parts. Once the sheath of Thorne is extended to protect the needle and its tip, Thorne teaches of no subsequent release of the sheath from being disposed to protect the needle and tip.

In the present invention, a shield is disposed about a needle and tip to provide protection. However, different from the teachings of Thorne, a temporary, releasible latch may be disengaged to permit the shield to refold and, thereby, permit reaccess to the needle for a subsequent medical procedure. Once each procedure is complete, the shield is again extended and latched to provide a safety cover. Further, an unreleasible lock is provided for the protective shield to thereby assure secured needle tip protection at the end of use.

In a preferred embodiment, the shield includes a needle guide, proximally disposed relative to the tip of a needle, which protects the tip, both, as the protective shield is displaced to cover and shield the needle and as the shield is removed to bare the needle for use. The needle guide is disposed and constrained to travel in alignment with the long axis of the needle, but constrained to facilitate movement of the shield about the needle without contacting the needle tip. Importantly, a preferred shield does not combine with the needle to form a substantially rigid body, but this shield is self contained in its ability to form a rigid body when extended to protect the needle. In conjunction with the guide, the shield provides protection without applying undue stress upon the needle.

Generally, the device may include at least two temporary or releasible latches. One latch constrains the shield to be disposed "out-of-the-way" when the needle is bared for use. A second releasible latch is latched when the shield is protectively disposed about the needle and needle tip. Further, the device and shield, in combination, include a permanent lock which is securely and unreleasibly affixed to prevent further use of the device when use is complete.

Other important factors in safety needle devices involve whether the device can be effectively used by a single hand and the number of times a needle may be accessed while being maintained in a needle-safe condition between uses. Especially in the case of hypodermic syringe needle devices, ability to access a medical needle from a safety state a plurality of times is very important as it is common practice to prefill a syringe using a needle to access a medical fluid containing vial and then deliver the contents of the syringe to a patient using the same needle.

As a manually activated needle shield, the invention provides for single handed operation and for access to a medical needle a number of times while protecting a user from inadvertent injury from the needle while protecting the needle and especially its fragile tip from damage when the device is moved to, displaced from or simply disposed within the safety of the shield.

However efficacious a needle shield may be, the needle which is so protected is still prone to cause inadvertent needle sticks when being used in standard needle bared procedures, such as occurs in hypodermic applications. It is for this reason that needleless systems have gained popularity. One important set of embodiments of this instant invention involves combining the needle shield with special connectors (or adapters) to provide functional access to the needle while retaining the needle under continual protective cover.

In such embodiments, each extended shield has a distally disposed latch which locks the extended shield in place as a prevention against inadvertent folding, to, thereby, protect against inadvertent baring of the needle and its tip. Each connector or adapter has an actuator and a key by which the latch is unlocked by the act of connecting the connector or adapter to the shield thereby permitting the shield to be removed (folded away) from the needle while keeping continuous protective cover about the needle tip. Cooperatively, as the shield is removed, motion of the connector or adapter toward the tip of the needle is in a linear path (which is in line with the long axis of the needle) toward and into the connector adapter. In this manner, there is practically no tendency to bend a needle during connector use. The needle tip is continuously protected by the shield until it is within the connector or adapter. As the needle tip is constrained to be covered and protected continually, needle safety is assured for all purposes in which a shield is used with a connector or adapter.

Such purposes are generally fulfilled by the same number and type of steps as would be required when performing the same function without using a connector or adapter. For this reason, most operations using these connectors cooperatively with shields are considered passive operations (i.e. they require no steps in addition to those of standard procedures without shields and connectors). Passive operation is further realized by interaction between the connector and shield to return the shield automatically to an extended needle protecting state as the needle is withdrawn from the connector. As in the case of connecting and folding the shield, the needle tip is continuously covered as the needle is extracted from the connector. The shield is thus assured to fully protect the needle before the connector is disconnected, assuring safety before, during and after needle use.

Within the scope of the invention, there are many applications where such connectors may be safely and efficaciously employed. For example, though not restricted to the following, connectors may be placed upon vials, "Y" connector sites on intravenous (IV) tubing sets and vacuum sampling tubes.

Accordingly, it is a primary object to provide a device having a safety shield for a medical needle and an associated sharpened tip which permits, within desirable and acceptable bounds of safety and efficacy, a plurality of cycles of shielding and baring the medical needle whereby the needle may be covered or otherwise shielded for transport or other non-needle use functions and then safely bared for use more than one time in a medical procedure.

It is an important object to provide a medical needle shield which is securely but releasibly affixed to cover and protect the medical needle and its associated sharpened tip in a first state.

It is another important object to provide a medical needle shield which is securely and unreleasibly affixed to cover and protect the medical needle and sharpened tip in a second state.

It is yet another important object to provide a needle guide which is disposed to operate within the shield to assure the sharp tip of the needle is untouched throughout each needle covering and baring procedure.

It is a particularly important object to provide a shield which is folded out-of-the-way in one state whereby a medical needle may be used in a medical procedure and which is unfolded to combine with the medical needle to form a substantially rigid needle shrouding structure which protects against inadvertent contact with a sharpened tip of the needle.

It is a very important object to provide a shield having two needle protective states, one of which is releasible to permit subsequent use of the needle and another of which is a locked state in which the shield is securely affixed to unreleasibly protect the needle tip.

It is also a very important object to provide a needle shielding device which is facilely operable by a single hand.

It is a fundamental object to provide a connector or adapter which has an actuator and a key which, when connectively coupled to a shield, selectively releases the shield from the releasible state and thereby provides access to the needle tip while providing protection against an inadvertent needle stick as the needle is displaced into and away from the shield.

It is another fundamental object to provide a connector or adapter which, in cooperation with the shield, provides passive access to the needle tip in a manner which requires a like number and type of steps necessary for using the needle and tip with a standard or non-safety needle system.

It is yet another fundamental object to provide a connector or adapter which, in cooperation with a needle shield, continuously provides protective cover for a needle tip as the needle is displaced through the connector or adapter.

It is an object to provide a connector for a vacuum sampling tube.

It is an object to provide a connector for a "Y" connection site used in such applications as IV lines.

It is an object to provide a connector for a drug or other medical vial.

It is an object to provide an adapter which protects against an inadvertent needle stick during percutaneous needle entry.

These and other objects and features of the present invention will be apparent from the detailed description taken with reference to accompanying drawings.

DETAILED DESCRIPTION OF THE ILLUSTRATED EMBODIMENTS

In this description, the term proximal is generally used to indicate relative nearness of a referenced item to a prospective user of a device, unless otherwise specified. The term distal is similarly used to indicate relative remoteness. Reference is now made to the embodiments illustrated in FIGS. 1–35 wherein like numerals are used to designate like parts throughout. In those cases where parts have similar, but not identical, form and function, numerals with primes may be used for ease in interpretative cross referencing.

Figure 1:
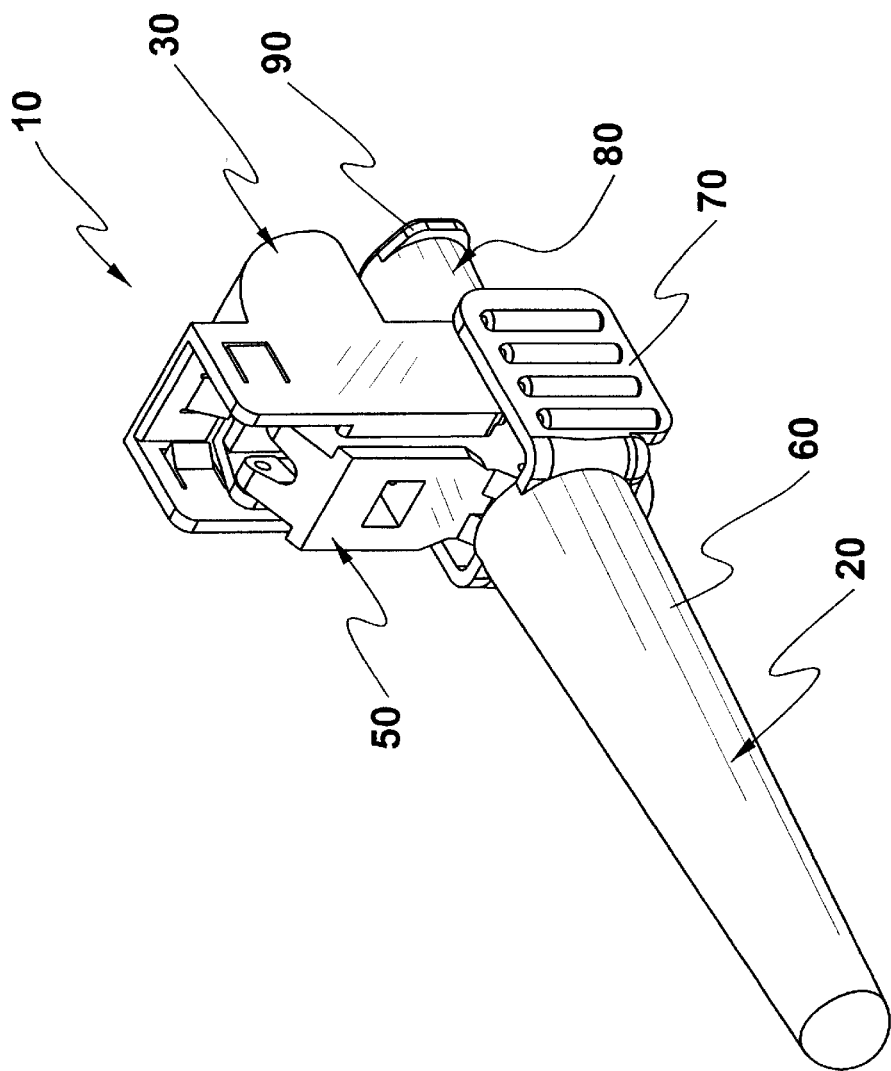
FIG. 1 is an embodiment of a medical needle shield assembly with a needle cover and a needle shield which permits reaccessing a medical needle, maintaining a protective cover over the needle between procedures requiring access to the needle and securely and permanently locking the shield to provide permanent needle protection once all desired procedures are complete.

A first embodiment of a needle shielding safety device, according to the invention, is seen in FIG. 1 as device 10. Device 10 has a needle cover 20 and a needle-hub-shield assembly 30.

Figure 2:
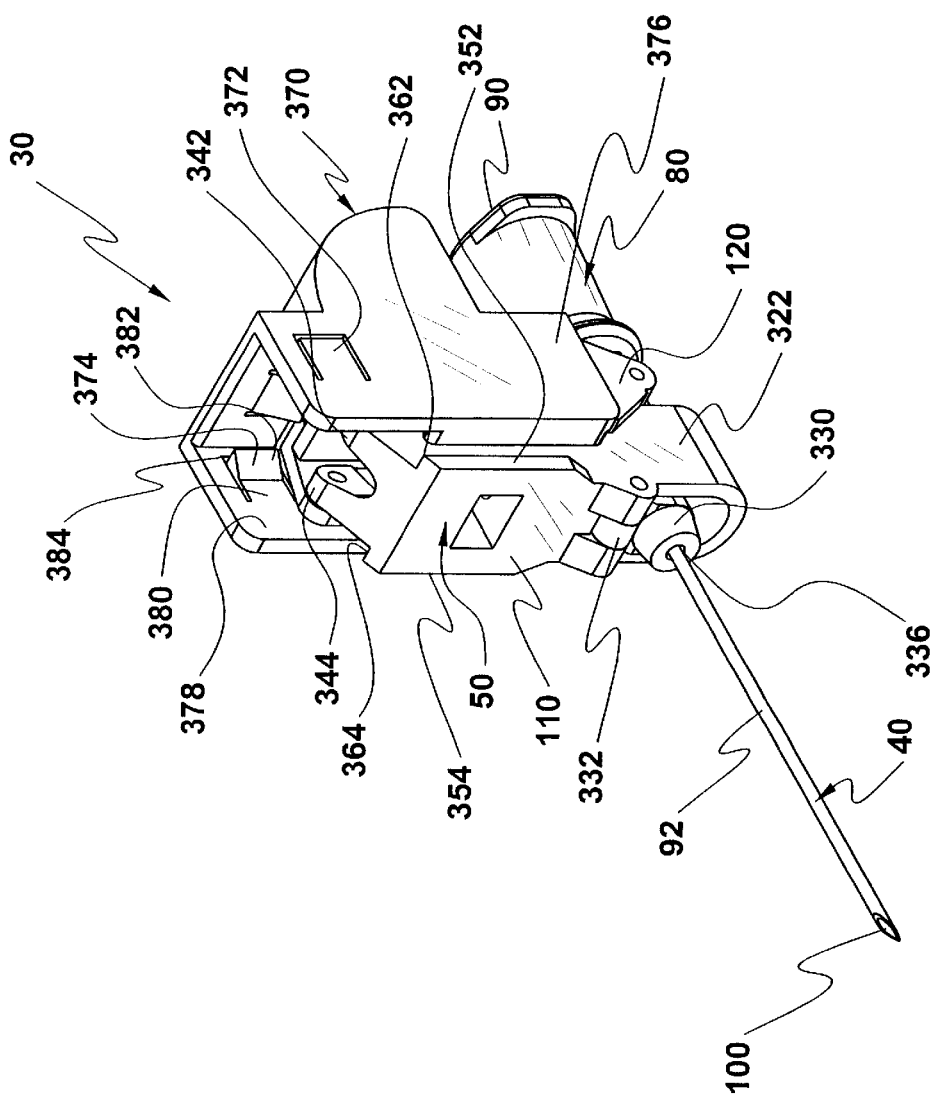
FIG. 2 is a perspective of the embodiment seen in FIG. 1 with the cover removed.

Needle-hub-shield assembly 30 is better seen in FIG. 2 where cover 20 is removed to expose a medical needle 40 and otherwise concealed distal portions of a foldable needle shield 50 to view. As is apparent from differences between FIGS. 1 and 2, needle cover 20 has an elongated hollow frustoconical distal part 60, which is similar in form and function to needle covers commonly used for protecting needles prior to use. Cover 20 also has a laterally and proximally disposed guard 70. Guard 70 acts as a keeper against inadvertent shield 50 actuation, before removal of cover 20 for use of needle 40. Similar to commonly currently available needle covers, needle cover 20 may be formed (e.g. injection molded) from polypropylene or other synthetic resinous material.

In addition to needle 40 and shield 50, assembly 30 has a needle hub 80 to which needle 40 is securely affixed and to which shield 50 is hingeably affixed. In this embodiment, hub 80 is seen to comprise a female luer(lock) fitting 90, though other flow through hub fittings and connections may be used within the scope of the instant invention. Needle 40 is generally formed having an elongated shank 92 and a sharpened tip 100.

It is important to note that for devices which permit reaccessing a medical needle, a cover such as cover 20 may not be necessary. When a shield is securely, but releasibly latched, a device, for example, such as assembly 30, may be deployed in a safe state with a needle 40 being protectively covered by a shield, such as shield 50, as disposed in FIG. 5. The device, so deployed, may then be packaged and shipped in an antiseptic protective wrap, such as a "bubble pack" without a cover, such as cover 20. Such deployment and elimination of a cover reduces both the cost of the basic device and the cost of discarding ancillary parts.

Primary to the inventive novelty of this embodiment is shield 50. As may be better seen in FIG. 4, shield 50 is formed as two segments, a distal segment 110 and a proximal segment 120. It should be noted that more than two segments may be used within the scope of the invention.

Distal segment 110 is made of a pair of juxtaposed elongated side pieces 322 and 324 and a closed end 326 which is formed to be contiguous with side pieces 322 and 324 to form a hollow needle tip 100 guard recess 328. Note that, as shield 50 unfolds to protect needle 40 and, especially, potentially fragile needle tip 100, tip 100 should make no contact with any parts of distal segment 110. Such contact could jeopardize the structural integrity of tip 100, and therefore, similarly jeopardize continuing use of needle 40. To assure that needle tip 100 is guided in and out of distal segment 110 in both cases where shield 50 is unfolded to become a shroud and refolded to bare needle tip 100 for further use, a needle bearing and guide 330 is affixed to side members 322 and 324 by a hinge 332. Needle bearing and guide 330 rotates relative to distal segment 110 via hinge 332 in a manner which displaces closed end 326 away from needle tip 100. Needle bearing and guide 330 comprises a needle bearing surface 336, best seen in FIGS. 2 and 7, by which needle 40 is constrained to assure needle tip 100 does not contact distal shield 50 as distal segment 110 rotates about needle 40 during folding and unfolding.

In addition, distal segment 110 has a pair of proximally disposed connective hinges 342 and 344 (see FIG. 2) by which segment 110 is hingedly affixed to segment 120. It should be noted that all or part of the hinges of assembly 30 may be formed as living hinges by injection molding all or any combination of parts of molding hub 80, proximal section 120 and distal section 110, if an appropriate material such as polypropylene is used, as is described in Thorne.

Located superiorly and proximally upon segment 110 are a pair of laterally extending wings 352 and 354 (see FIG. 2). Each wing 352 and 354 is displaced away from respective sides 322 and 324 (see FIG. 4) to provide a ledge, respectively numbered as 362 and 364, which acts as a catch for a releasable latch. Operation of such a catch and latch combination is disclosed in detail hereafter.

An important element of assembly 30 is a slideable latch part 370, seen in FIGS. 2, 4–6 and 8. Latch part 370 is slideably affixed to proximal segment 120 and comprises latches for both releasible and unreleasible connections to segment 110 when shield 50 is variably selectively extended to protect needle tip 100. As seen in FIG. 2, latch part 370 has two latches 372 and 374, each disposed in a respective side wall 376 and 378 of part 370. Latch 374 is formed integral with side wall 378 having a connecting riser 380, an inwardly sloping surface 382 and a bearing surface 384. Latch 372 is formed as a juxtaposed mirror image of latch 374. The details of latch 372 are not seen in the figures, but its riser, inwardly sloping surface and bearing surface are similar to connecting riser 380, inwardly sloping surface 382 and a bearing surface 384 of latch 374 and are numbered for reference in this text as 380', 382' and 384', respectively. Note that bending of risers 380 and 380' as sloped surfaces 382 and 382' meet wings 352 and 354, respectively, permits part 370 to be "snapped" onto segment 110 during an assembly process.

Figure 7:
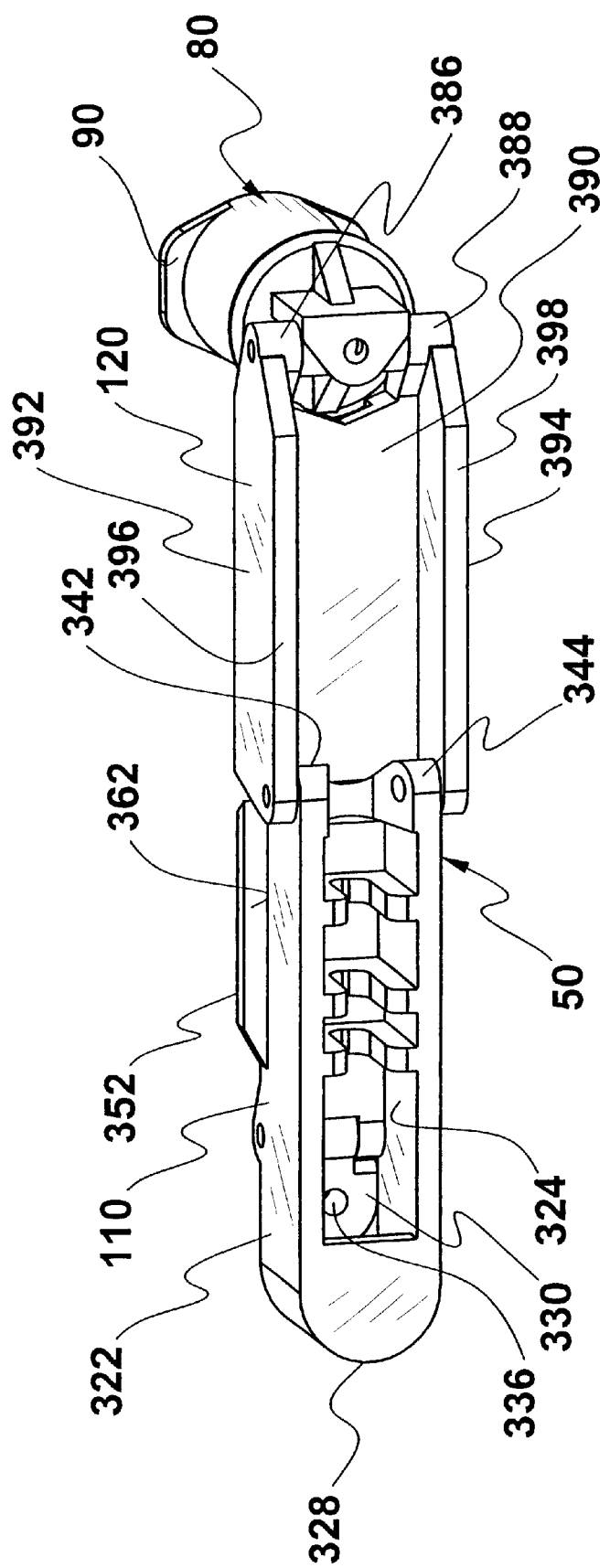
FIG. 7 is a perspective of an inferior view of a needleless folding portion of the shield seen in FIGS. 1–6.

Reference is now made to FIG. 7 where detailed structure of proximal segment 120 is more clearly seen. As well as being connected to distal segment 110 by hinges 342 and 344, proximal segment 120 is also connected to needle hub 80 by a pair of hinges 386 and 388. As previously indicated, hinges such as hinges 342, 344, 386 and 388 may be molded as living hinges should any combination of distal segment 110, proximal segment 120 and/or needle hub 80 be molded as integral parts. In such a case, parts may be molded from polypropylene. Proximal segment 120 further is preferably formed as a unitary structure having a planar top joining layer 390 and two side members 392 and 394 orthogonally affixed thereto. Each side member forms a linear rail, respectively numbered 396 and 398, disposed away from layer 390.

Figure 8:
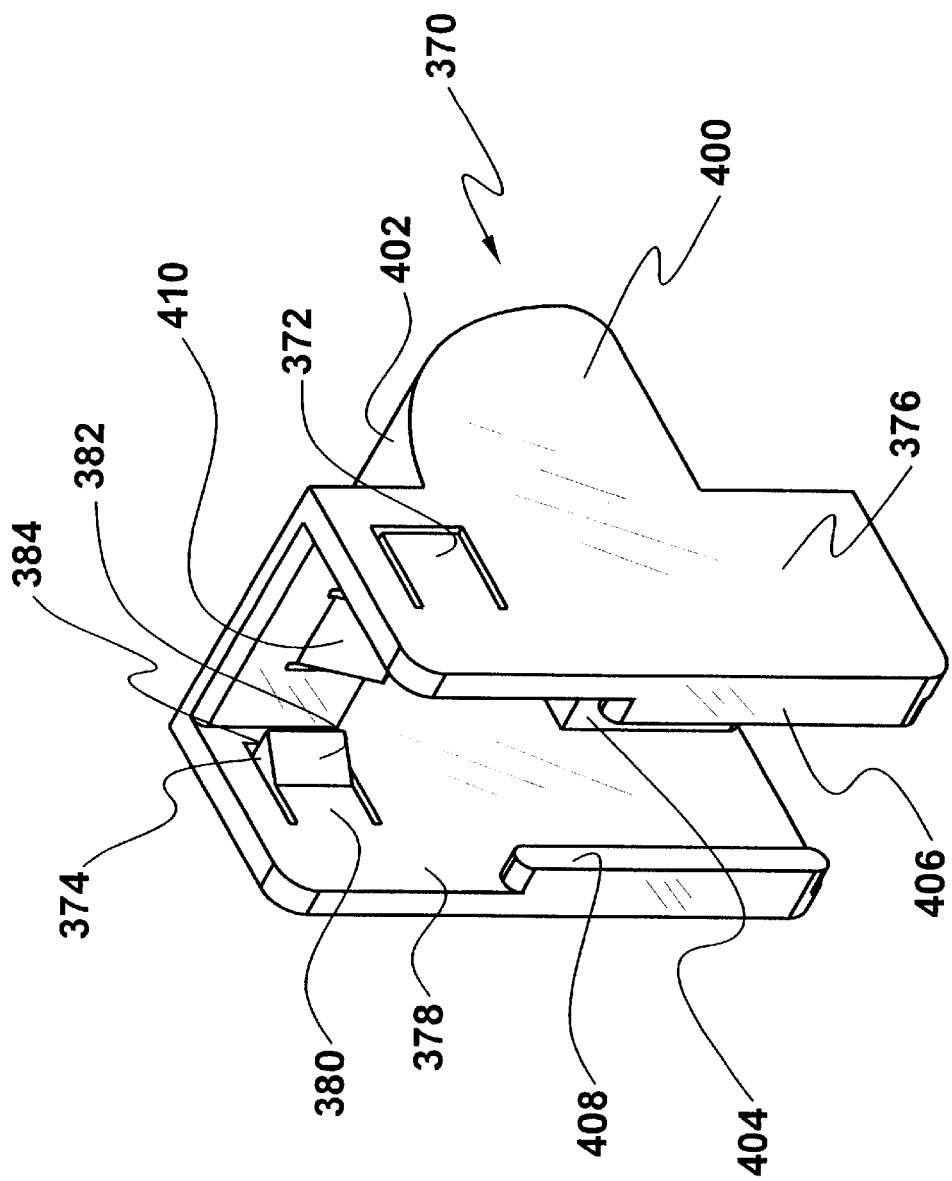
FIG. 8 is a perspective of a slider portion of the needle shield.

As best seen in FIG. 8, latch part 370 has a button part 400 which is formed on a generally superiorly disposed side of latch part 370. On each side, button 400 is integral with side walls 376 and 378. Further, button 400 comprises a raised surface 402 which provides a digitary interface which permits latch part 370 to be slid proximally to release latches 372 and 374 from contact with wings 352 and 354, respectively, to permit folding of distal segment 110 against proximal segment 120 to bare needle 40 for use. Contact with the same raised surface 402 permits button 400 to be used as an actuator to unfold distal segment 110 and proximal segment 120 about needle 40 to provide a protective cover for needle tip 100. Distally displacing part 370 slideably affixes surfaces 384 and 384' (as earlier cited 384' is not found in the figures) against wing surfaces 364 and 362, respectively, to provide a releasible, but secure fastening of part 370 about hinges 342 and 344, thereby assuring a stable, substantially rigid structure.

Note that part 370 should remain slideably affixed to proximal segment 120. For this purpose, part 370 comprises a substantially planar understructure 404 generally disposed inferior to button 400. Understructure 404 is sized to accommodate layer 390 such that part 370 slides facilely thereupon. Side walls 376 and 378 are integral with understructure 404 as well as button 400. Opposite understructure 404 each side wall, 376 and 378, terminates in a ledge, numbered 406 and 408, respectively. Side walls 376 and 378 and ledges 406 and 408 are sized and disposed such that part 370 slides upon layer 390 and rails 396 and 398. In this manner, part 370 is proximally displaced to free latch connections formed by latches 372 and 374 and wings 352 and 354 and distally displaced to engage those latch connections.

Figure 5:
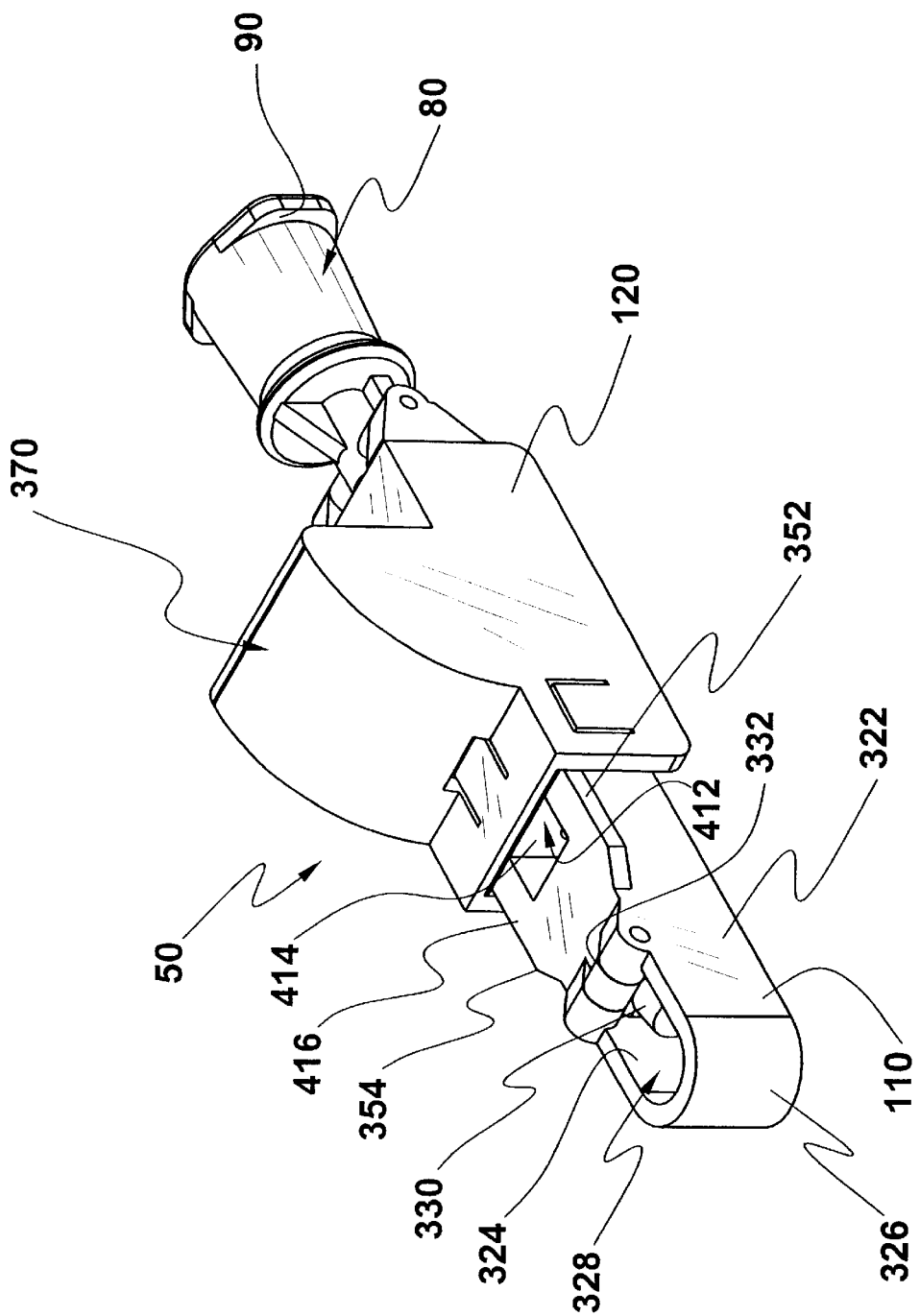
FIG. 5 is a perspective of the device as seen in FIGS. 2 and 4, with the shield fully displaced to provide protective needle coverage, but disposed such that the shield may be retractively displaced to provide repeated needle access.

Formed in understructure 404 is another latch 410 (see FIG. 8). A catch 412 for latch 110 is formed as a rectangular slot 414 in a superior portion 416 of distal segment 110 between wings 352 and 354 as seen in FIG. 5. Latch 410 is disposed to be urged outwardly and then reactively snap into slot 414 as part 370 is fully displaced distally to achieve any unreleasible coupling thereby securely affixing a protective shield about needle tip 100.

Figure 4:
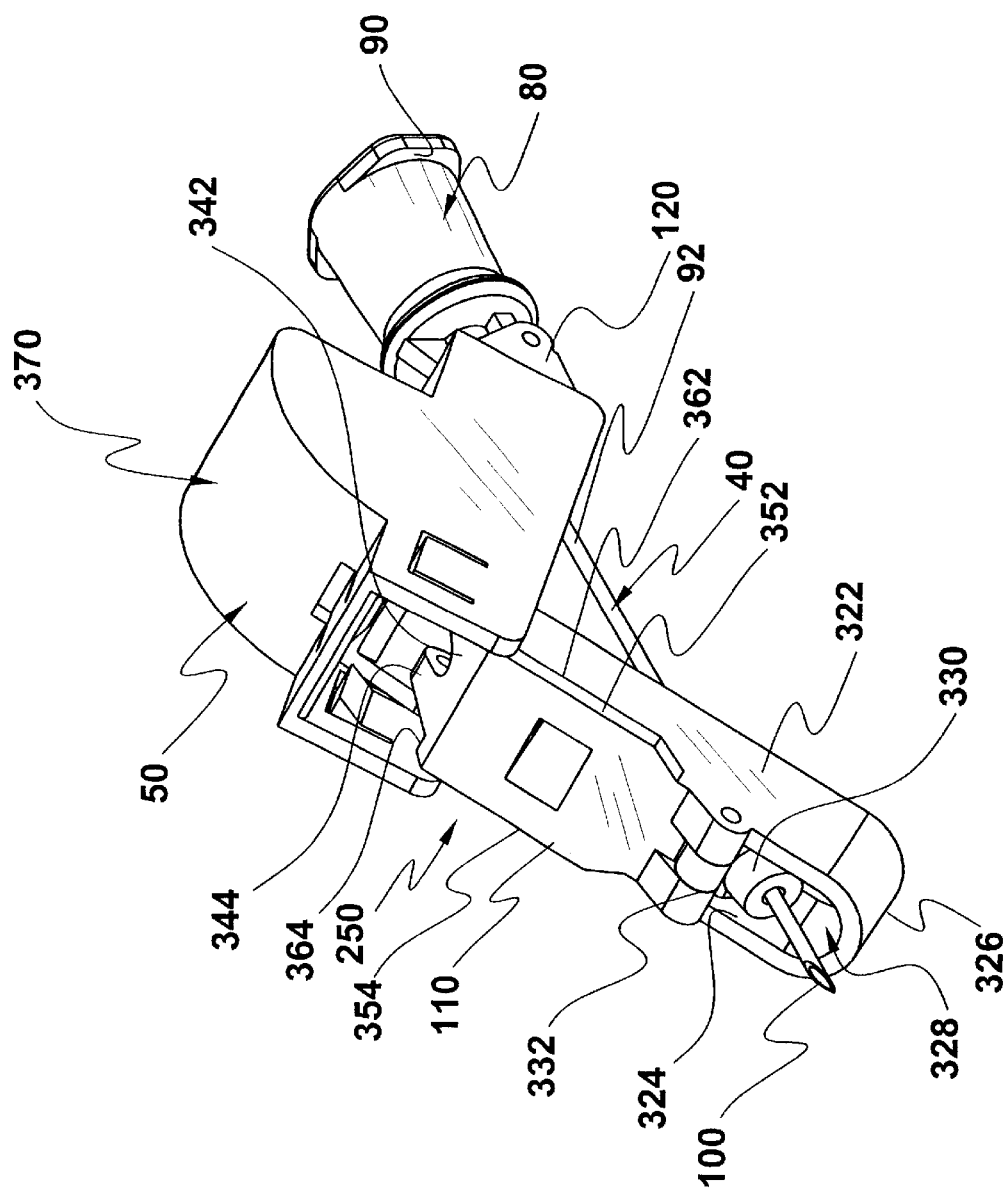
FIG. 4 is a perspective of the device as seen in FIG. 1, with the shield partially displaced.
Figure 6:
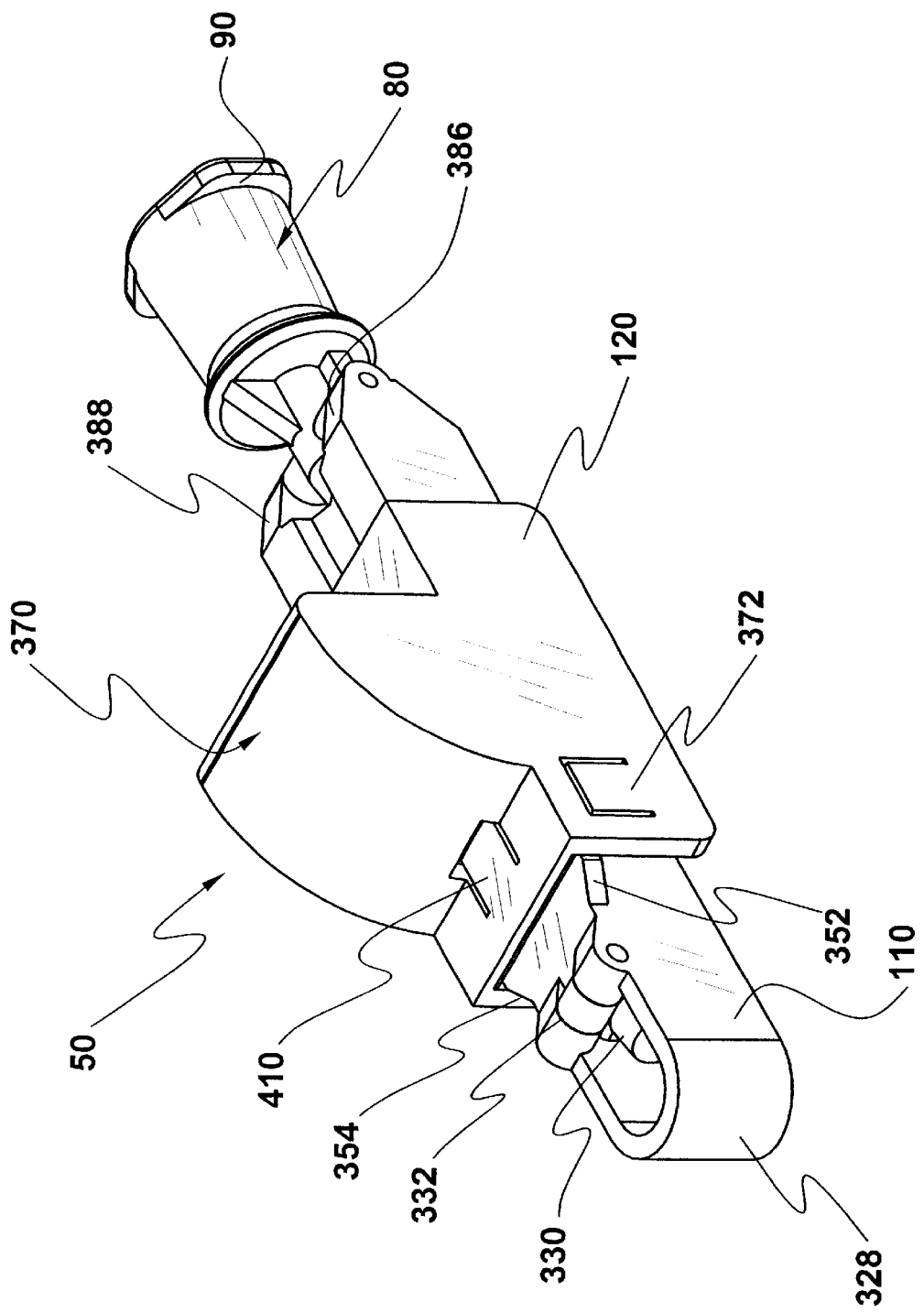
FIG. 6 is a perspective of the device as seen in FIG. 5, but with a part of the shield displaced to unreleasibly lock the shield to prevent needle reaccess.

Shield 50, therefore, provides a means for reaccessing a medical needle from a shrouded state within a releasible shield and for recovering the needle to the releasibly latched shrouded state a plurality of times to improve safety in medical procedures involving multiple separate uses of the needle. Once the total medical procedure is completed, the medical needle can be unreleasibly locked within the shield. Note in FIG. 5 shield 50 is releasibly disposed about needle 40 (not seen in FIG. 5). In FIG. 4, shield 50 is partially displaced and then, in FIG. 2, shield 50 is fully displaced to bare needle 40 and needle tip 100. In a similar manner, shield 50 may be displaced from the state seen in FIG. 2 through the state seen in FIG. 4 to the safety, needle covering state seen in FIG. 5. This sequence may be repeated as desired throughout a medical procedure. Finally, distal displacement of part 370, as seen in FIG. 6, engages latch 410 in slot 414 (seen in FIG. 5) and thereby securely and unreleasibly locks shield 50 about needle 40.

Figure 3:
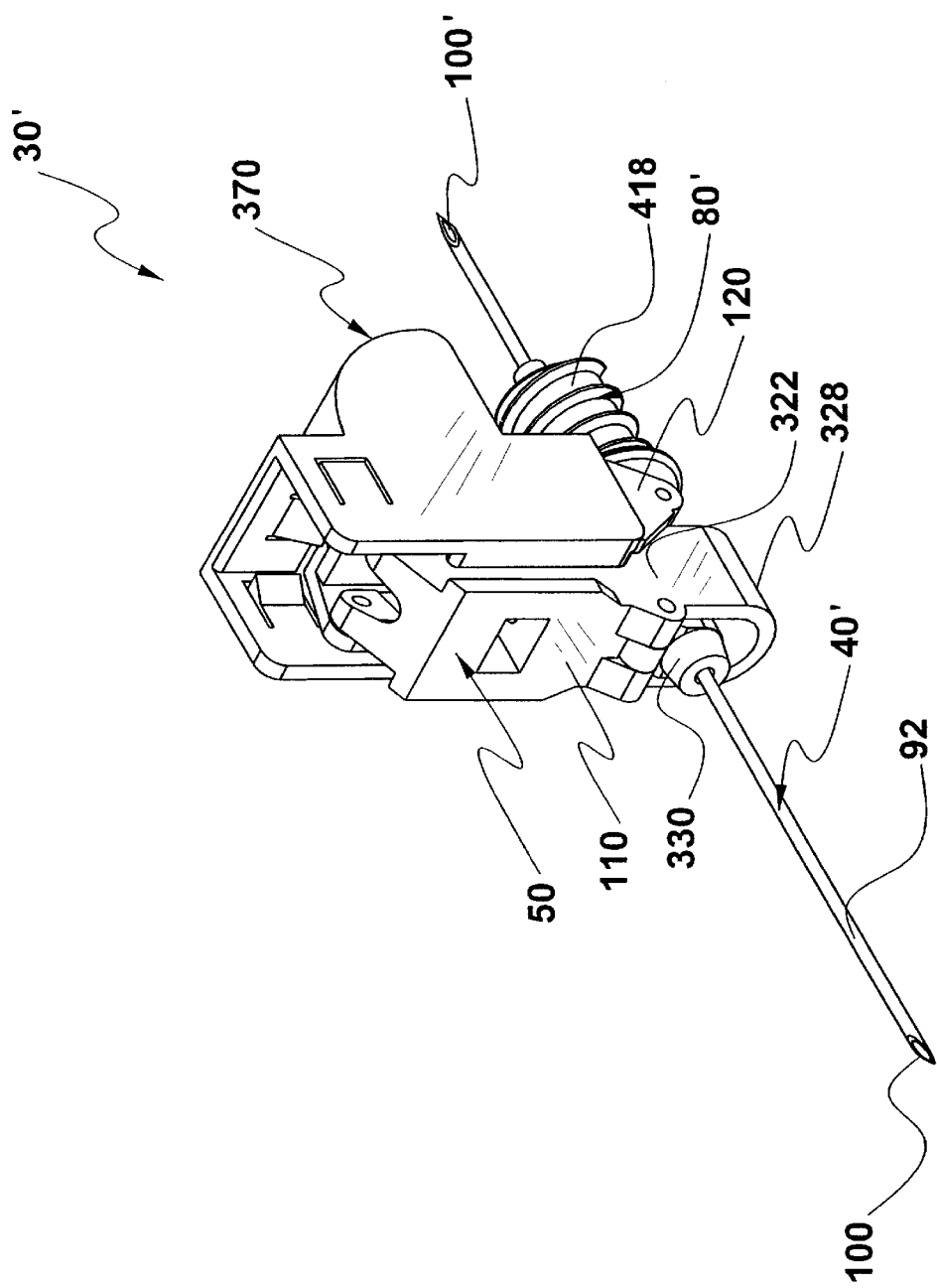
FIG. 3 is a perspective which is similar to the perspective seen in FIG. 2 with a variation of having a needle with two sharpened ends and a threadable needle hub, such as those medical needles used in phlebotomy.

In another embodiment 30', shield 50 may be employed with a needle 40' having two sharpened ends, 100 and 100', as seen in FIG. 3. In this case, a hub 80' has a threaded connection 418 which may be used with a phlebotomy barrel for the purpose of drawing fluid samples into a vacuum sampling tube.

Figure 9:
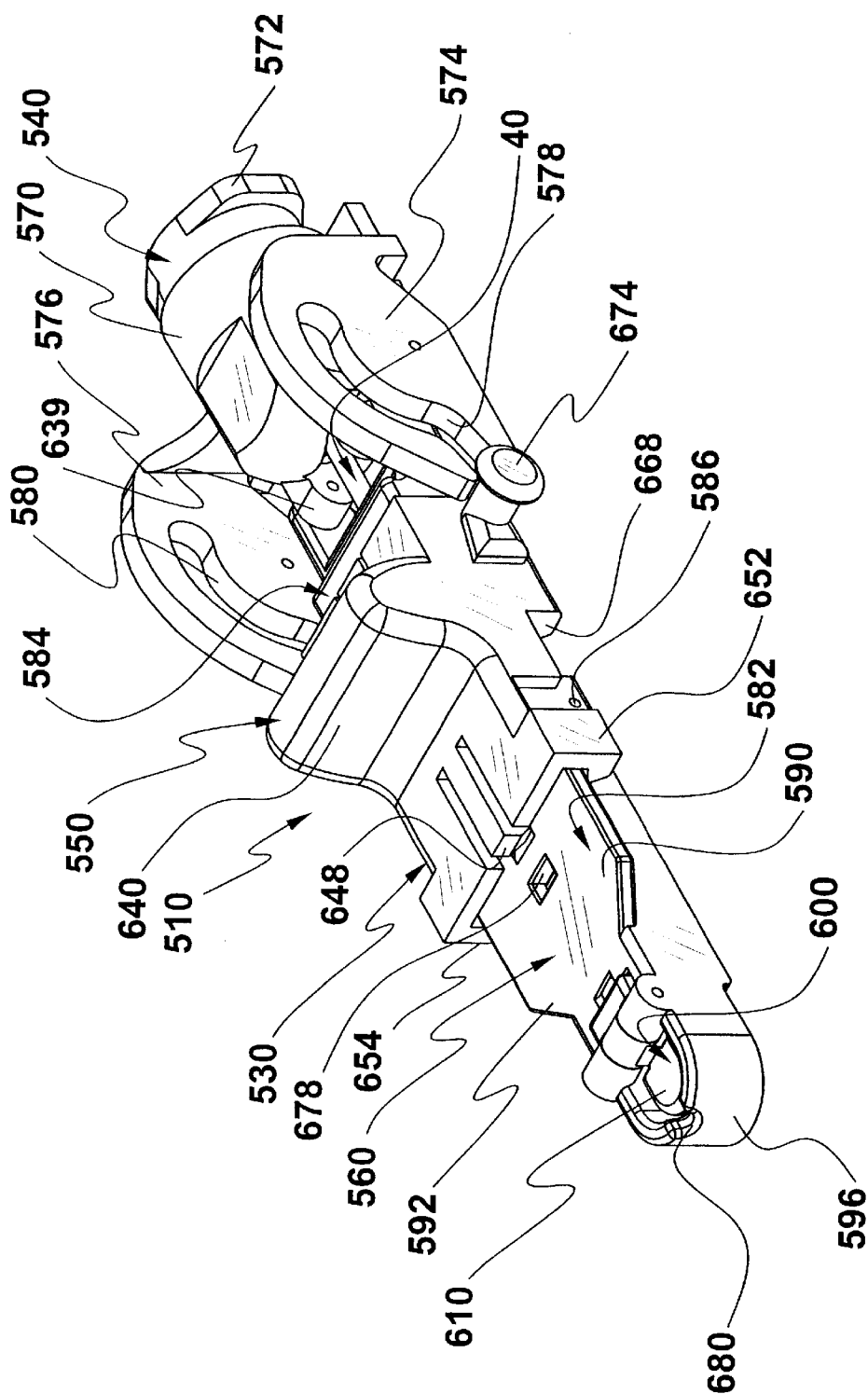
FIG. 9 is a perspective of yet another embodiment of the instant invention showing a shield protectively disposed about a medical needle, this embodiment having both releasible and unreleasible catches which are selectively engageable when the shield is protectively disposed about the needle.

A device 510 which is yet another embodiment of the instant invention is seen in FIG. 9. Device 510 includes a shield assembly 530 which is hingedly affixed to a hub assembly 540. Shield assembly 530 is generally fabricated from two parts, a slider 550 and a needle shield 560. Hub assembly 540 includes a medical needle, such as needle 40 (earlier enumerated), securely affixed to a hub part 570. Hub part 570 is shown to comprise a proximal female locking luer connection 572 (similar to luer fitting 90) for connecting device 510 to a syringe, although other hub connections can be used within the scope of the invention.

Associated with hub part 570 is a pair of juxtaposed slider guides 574 and 576 which are aligned with the long axis of needle 40. Each guide 574 and 576 has a guide track 578 and 580, respectively, the purpose of which is described in detail hereafter.

Figure 10:
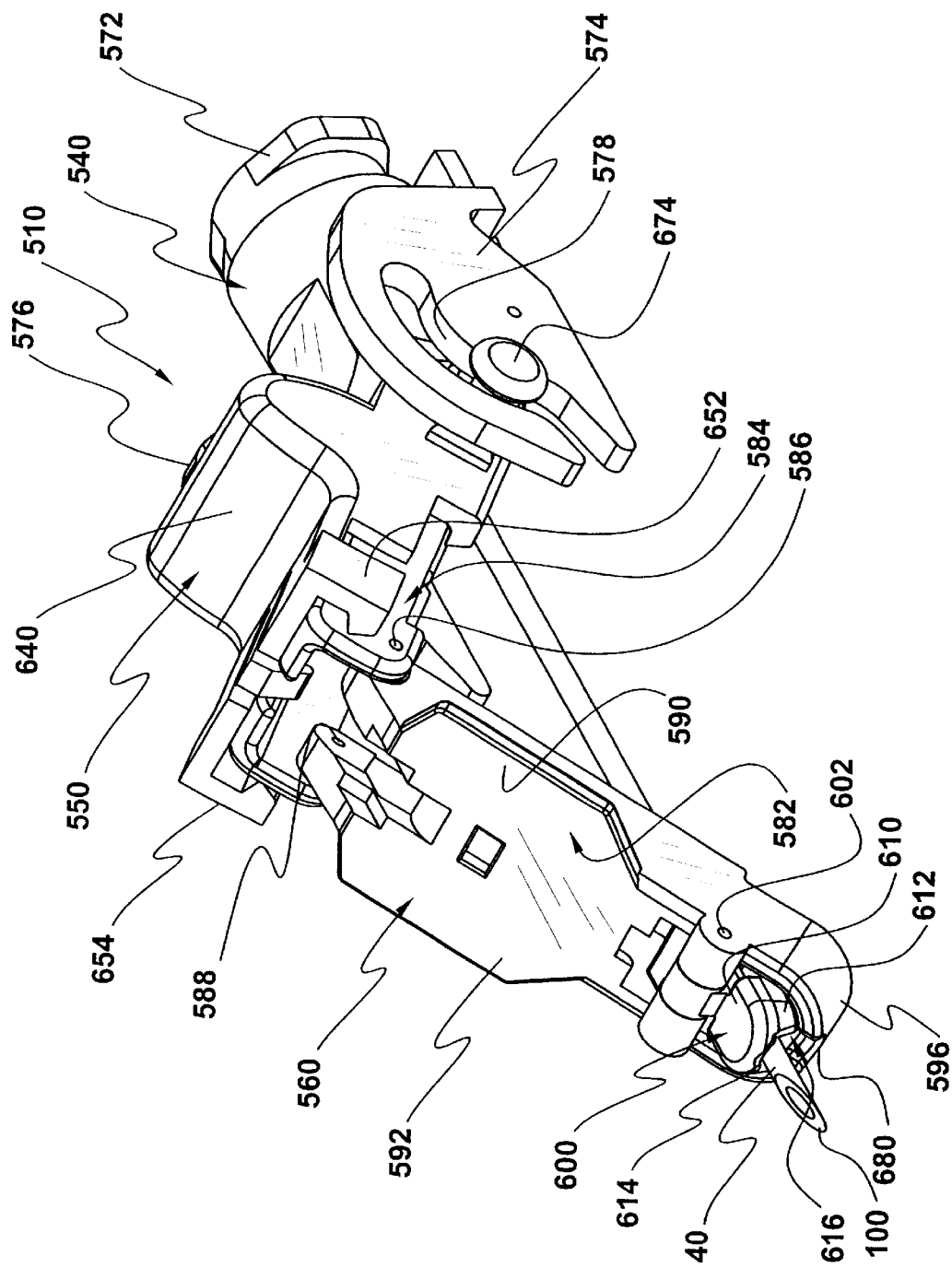
FIG. 10 is a perspective of the device seen in FIG. 9 wherein the shield is partially displaced to bare a sharpened tip of the medical needle.

Shield 560 is formed having a pair of hinged, substantially rigid arms 582 and 584, which are better seen in FIG. 10. Note that arm 582 is affixed to arm 584 by hinges 586 and 588. Of course, hinges 586 and 588 may be living hinges interconnecting arms 582 and 584 when integrally formed in the same mold cavity with arms 582 and 584. With the exception of needle 40 and any adhesives used to affix needle 40 to hub part 570, all other parts may be made from synthetic resinous material, an example of which is polypropylene. Though other materials may be used, it is preferred that material be selected which has sufficient rigidity to shield needle 40 and flexibility to form living hinges.

Arm 582 has a pair of superiorly disposed laterally extending wings 590 and 592 which form catches for slider 550, as described in detail hereafter. Distal from wings 590 and 592, a needle guide 600 is affixed to a distal portion of arm 582 by a hinge 602. Distal from guide 600, arm 582 has a closed end 596 to protectively cover a tip 100 of needle 40 when shield 560 is extended about needle 40. In the same manner that hinges 586 and 588 may be integrally molded as part of shield 560, hinge 602 and associated needle guide 600 may be molded as an integral part of arm 560 and shield assembly 530.

Figure 16:
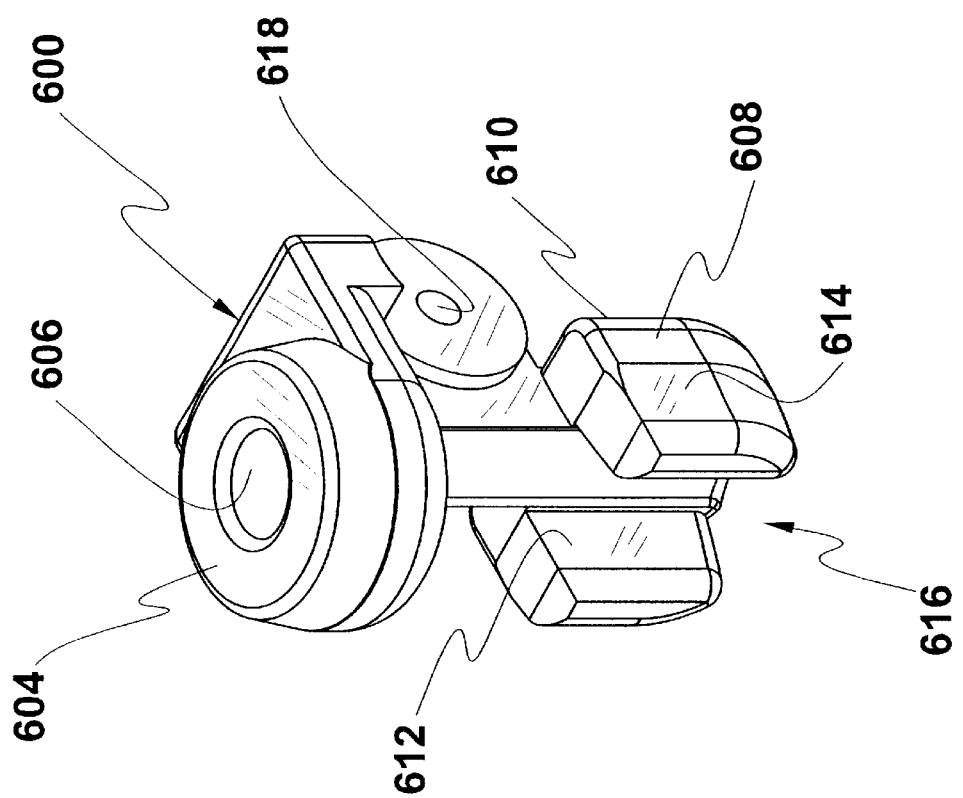
FIG. 16 is a perspective of a needle guide associated with the shield.

Needle guide 600 is seen in FIG. 16 as a separate part for clarity of presentation. Guide 600 has a proximally disposed guide ring 604 which has a medially disposed through hole 606, sized for facile passage of needle 40 (not shown in FIG. 16). Note that ring 604 should be disposed geometrically to constrain and guide needle 40, as shield 560 is folded to bare needle 40, in such a manner that tip 100 does not touch any part of shield 560, especially arm 582. In this manner, tip 100, which may be fragile and prone to being damaged, is guided to move past end 596 without being touched. Needle guide 600 also has a distally disposed shroud 608, having a cover part 610 and a pair of side protectors 612 and 614. Note, that cover part 610 in combination with side protectors 612 and 614 define an opening 616 through which needle 40 glides as shield 560 is folded and unfolded. Needle guide 600, when formed as a separate part, has a transverse through hole 618 disposed for use in hinge 602.

Figure 14:
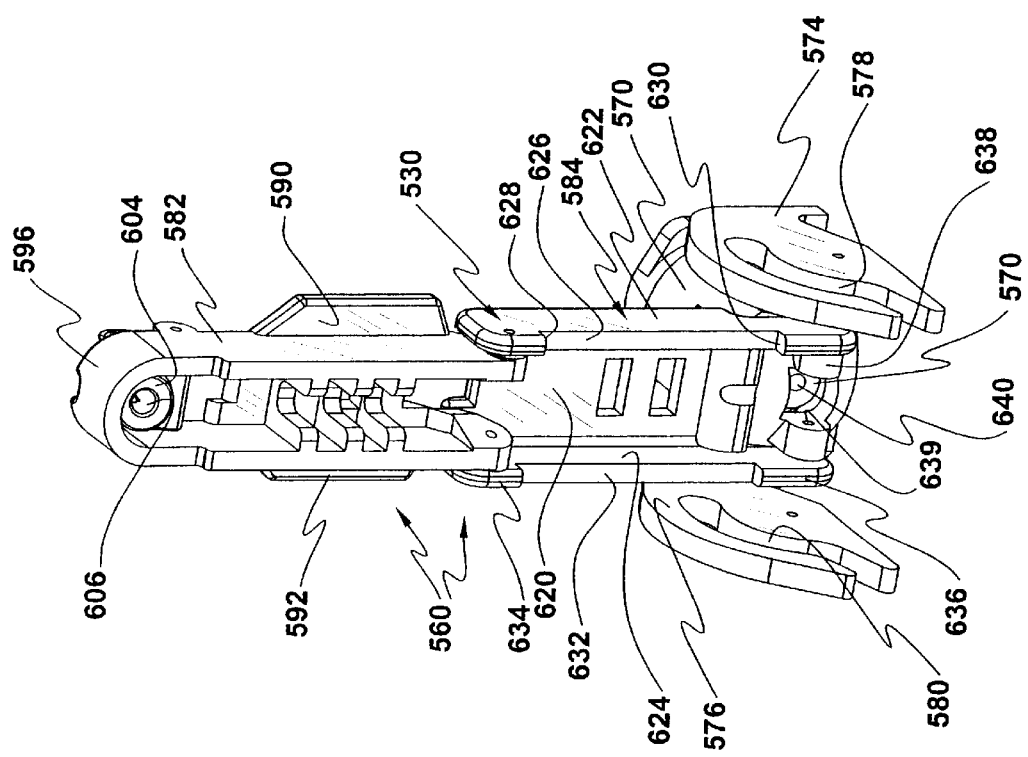
FIG. 14 is a perspective of a portion of the shield of the device seen in FIG. 9 disposed in an "as molded" state.

Arm 584 is best seen in FIG. 14, where shield assembly 530 is seen in a bottom view, without needle 40 to portray a potential "as molded" orientation. Arm 584 has a substantially planar, medially disposed top portion 620 with a pair of inferiorly distending sides 622 and 624. Side 622 has a substantially planar bottom surface 626 disposed between a pair of inferior extensions 628 and 630. Similarly side 624 has a substantially planar bottom surface 632 and a pair of inferiorly oriented extensions 634 and 636.

A pair of hinges 638 and 639 (see FIG. 14) hingedly affix arm 584 to hub 570. Note that, as disposed in FIG. 14, shield 560 and hub 570 may be injection molded as a single, integrally molded part. It may also be noted that hub 570 has a medially disposed through hole 640 wherein needle 40 is affixed.

Figure 15:
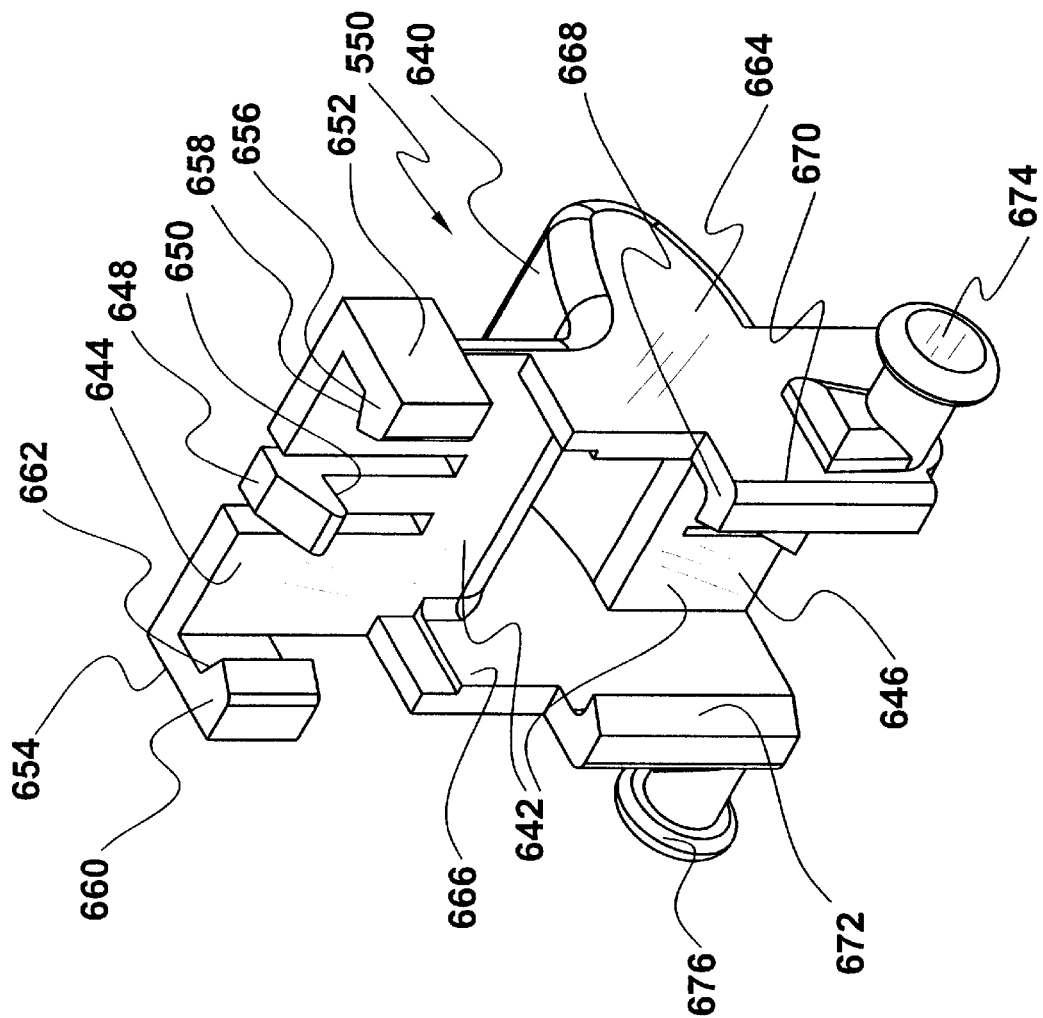
FIG. 15 is a perspective of a slider part associated with the shield.

Reference is now made to FIG. 15 wherein slider 550 is seen as a separate part. Slider 550 is used as an actuator in folding, in unfolding, in temporarily latching and unreleasibly locking shield assembly 530. As disposed for use on shield assembly 530, slider 550 has a superiorly extending button 640 which acts as an actuator for shield assembly 530. Button 640 should be configured for facile distal and proximal application of force to displace shield 560 to a folded state from an unfolded state and to an unfolded state from a folded state. Such configurations are well known in the actuator manufacturing art. Button 640 is an integral part of a top section 642 of slider 550, which has a distal top section 644 and a proximal top section 646.

Distal top section 644 has a medially disposed latch leg 648 which has an inferiorly disposed latching face 650.

Distending inferiorly on each side of top section 644 are a pair of latching legs 652 and 654. Latching leg 652 has a medially directed latch 656 with a superior latch face 658. Latching leg 654 similarly has a medially directed latch 660 and a superior latch face 662.

Proximal top section 646 is integrally connected to two parallel sides 664 and 666 which distend inferiorly therefrom. Side 664 abruptly ends inferiorly in a medially extending slide rail 668 which extends medially from an inferior face 670 of side 664. Side 666 has a similar, but mirror image slide rail 672. In addition, side 664 has an outwardly extending guide knob 674 disposed proximally and inferiorly relative to button 640. Side 666 has a similarly positioned guide knob 676.

Referring to FIG. 9, slider 550 is assembled as a part of shield assembly 530 by snapping slider sides 664 and 666 (see FIG. 15) about respective inferiorly distending sides 622 and 624 (seen in FIG. 14), respectively, until respective surfaces 626 and 632 are juxtaposed slide rails 668 and 672. In this manner, slider 550 is constrained to slide along arm 584 with slide rails 668 and 672 travel limited by extensions 626 and 630 and 634 and 636 (see FIG. 14), respectively. In similar fashion, as seen in FIG. 9, latching leg 652 is latched upon a catch formed by wing 590 and latching leg 654 is latched upon a catch formed by wing 592. Note that a slot 678 is medially disposed in the top surface of arm 582 in line with latch leg 648. Function of slot 678 relative to latch leg 648 is described hereafter.

FIG. 9 displays a state of device 510 which may be used in transport and storage of device 510 before use. In this state, needle 40 and needle tip 100 are safely covered and protected by shield 560 which is constrained to be a substantially rigid member by the combination of guide 600, shield 560 and slider 550 which is disposed and securely latched about hinges 586 and 588 by interaction of wings 590 and 592, latching legs 652 and 654, distending sides 622 and 624 and slide rails 668 and 672 as previously disclosed. Note at this point of rotation, part 610 provides a protective superiorly disposed cover for needle tip 100. In this state, device 510 may be packaged in a "bubble pack" or the like package to protect cleanliness and sterility of needle 40 during transport and storage.

After removal of device 510 from protective packaging and affixing needle 40 to a syringe or the like for use, slider 550 may be displaced toward luer connection 572, preferably by applying a proximally directed force against button 640, until latching legs 652 and 654 are freed from catches formed by wings 590 and 592, respectively, as seen in FIG. 10. Continuing displacement of slider 550 causes knobs 674 and 676 to enter and follow tracks 578 and 580, respectively. Tracks 578 and 580 are formed to urge slider 550 and affixed arm 584 to rotate about hinges 638 and 639 (see FIG. 14) and thereby cause shield 560 to fold about needle 40. Attention should be paid to a recess 680 disposed in distal end 596 of arm 582. Recess 680, while blocked by cover part 610 when shield 560 is unfolded, provides a clear pathway for needle tip 100 to exit shield 560 without contacting any portion of the shield. It is important to note that guide ring 604 (see FIG. 14) is positioned to be continuously proximally disposed relative to tip 100 during all phases of transport and storage and is displaced proximally away from tip 100 during unfolding to assure tip 100 has no contact with any portion of shield 560.

Figure 11:
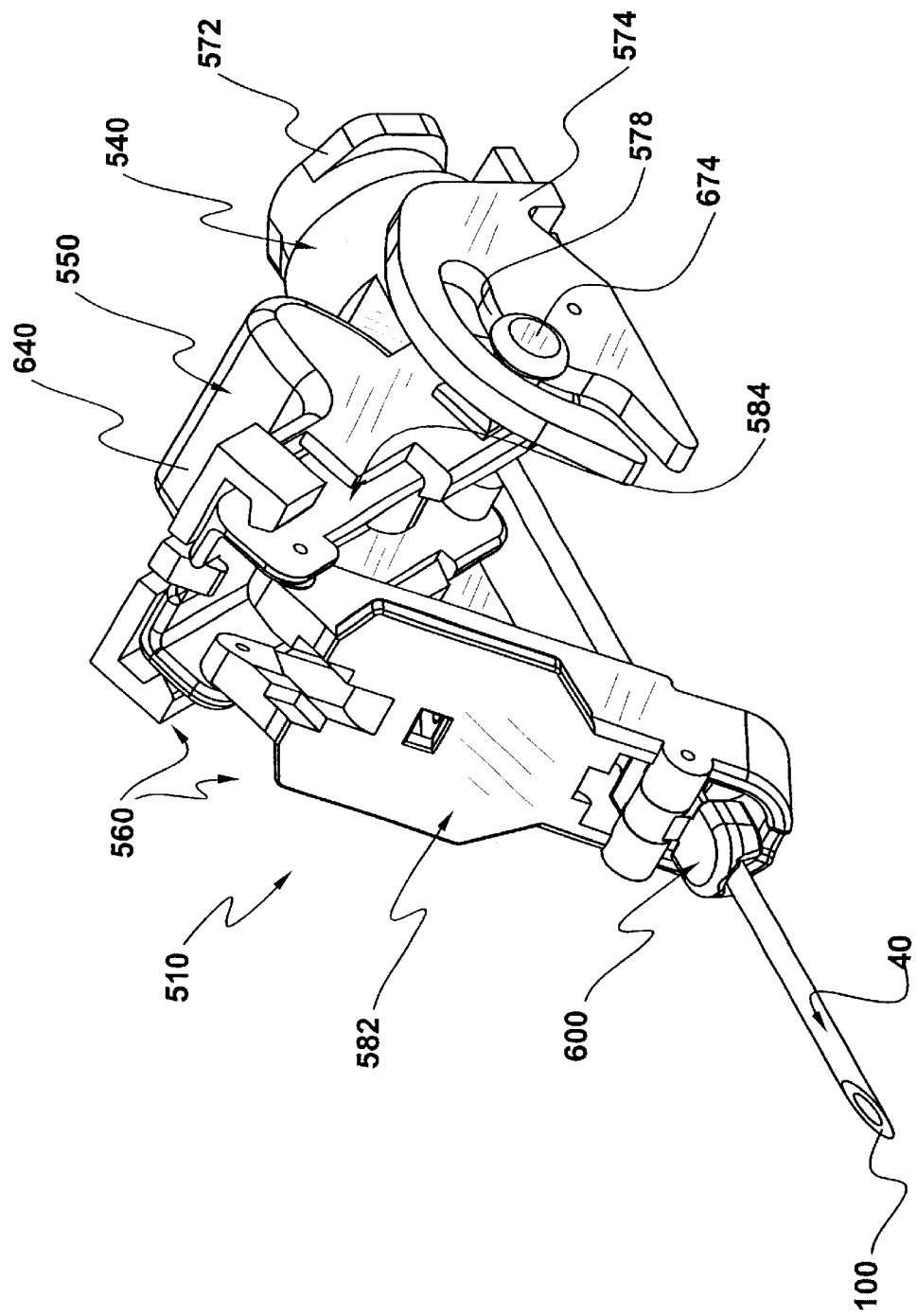
FIG. 11 is a perspective of the device seen in FIG. 9 wherein the shield is displaced more than the displacement seen in FIG. 10 to bare more of the sharpened tip of the medical needle than in FIG. 10.

Continued rotational displacement of button 640 with knobs 674 and 676 following tracks 578 and 580 continues to pivot arm 584 and further fold arm 582 as seen in FIG. 11.

Figure 12:
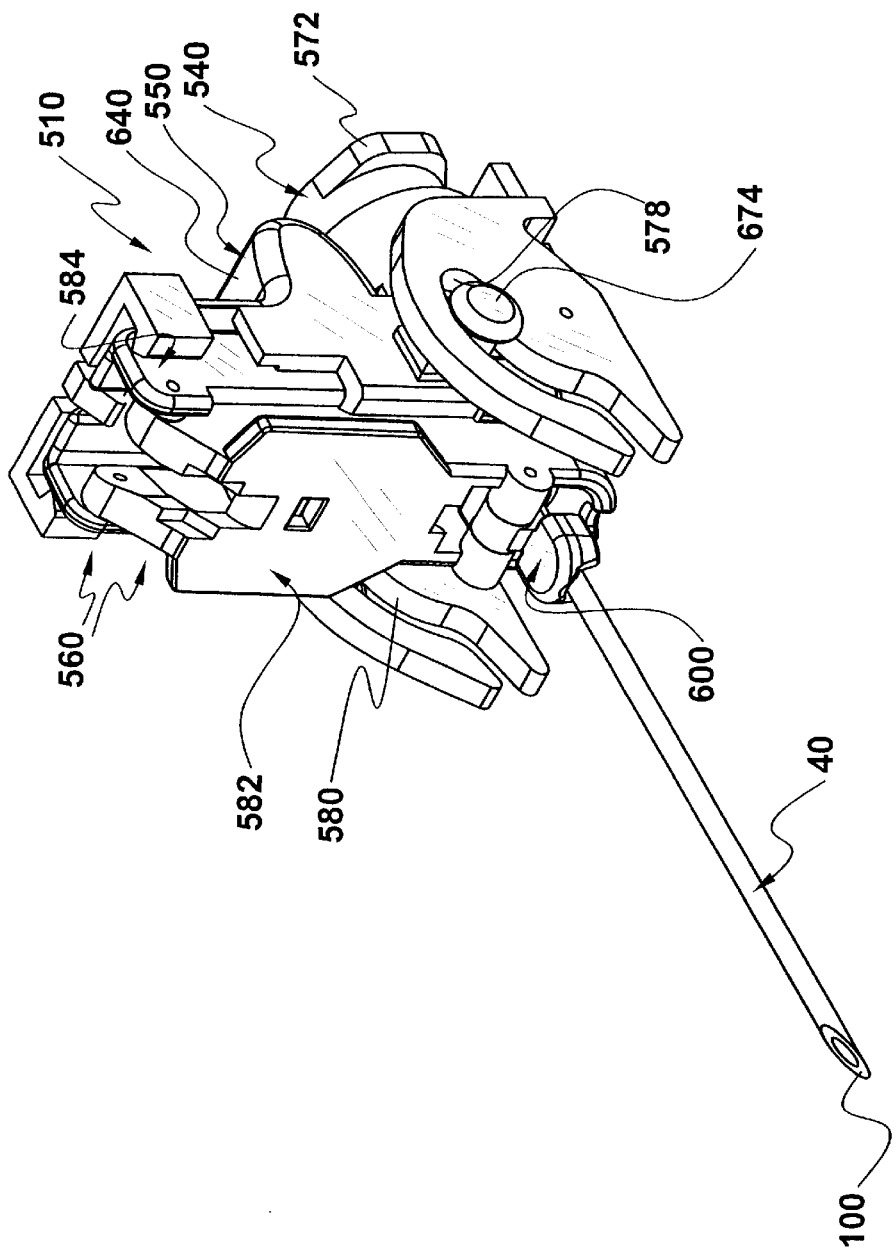
FIG. 12 is a perspective of the device seen in FIG. 9 wherein the shield is fully folded to altogether bare the needle and needle tip.

Ultimately, shield 560 is completely folded to bare needle 40 for use as seen in FIG. 12. It is preferred to provide releasible latching tabs (not shown) which may be affixed to react between fixed elements of device 510 and folding parts (e.g. guide 574 and slider 550) to retain shield 560 in a state of relative stability while folded.

From the state seen in FIG. 12, shield 560 may be unfolded to protectively cover needle 40 and particularly needle tip 100 by applying a distally directed force against button 640. In this manner, shield 560 unfolds sequentially through states seen in seriatim in FIG. 11 then FIG. 10 until completely disposed in a releasibly latched state in FIG. 9. Needle 40 may be reaccessed and then recovered a plurality of times by following the steps outlined above to uncover and recover needle 100.

Figure 13:
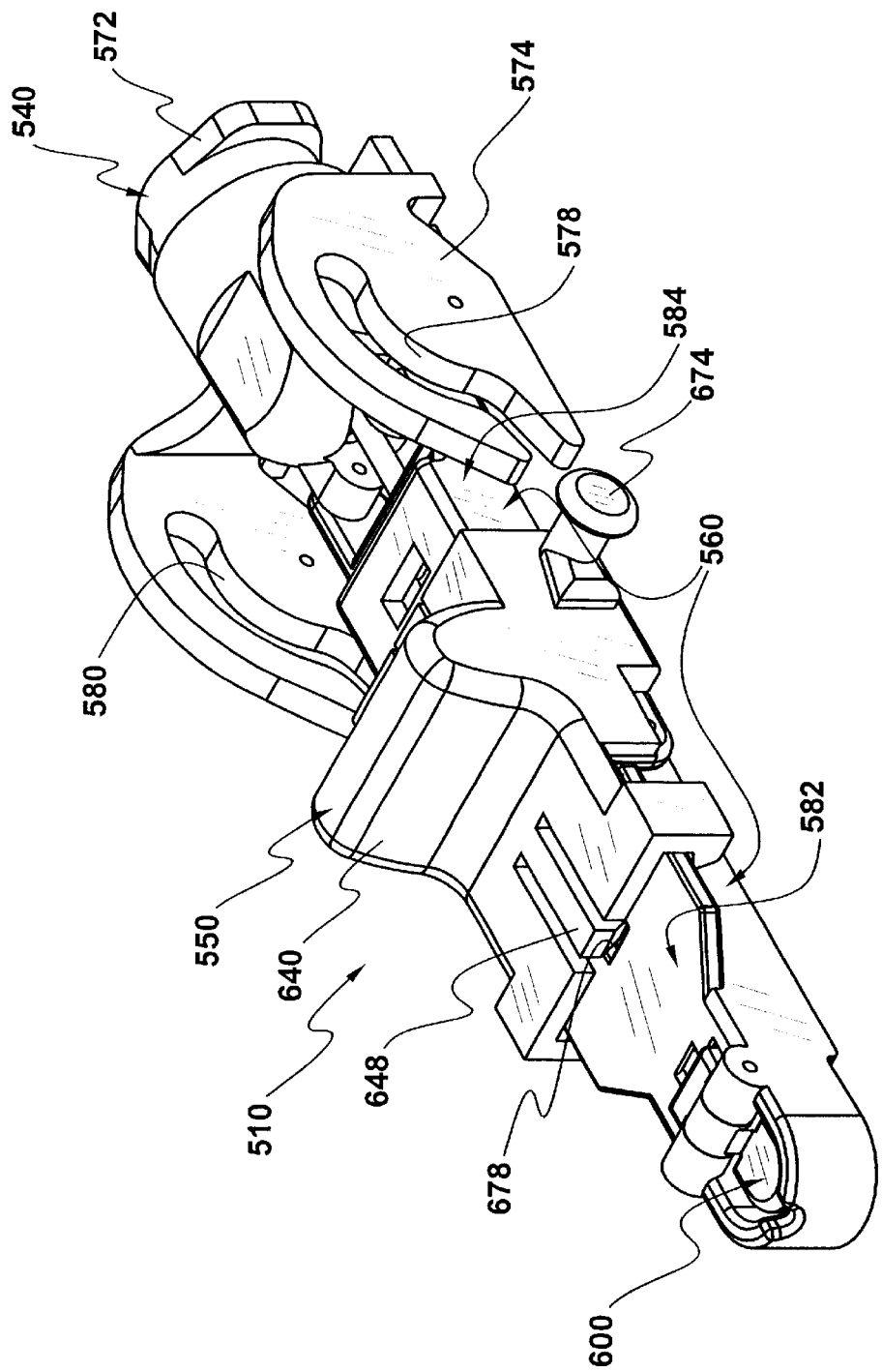
FIG. 13 is a perspective of the device seen in FIG. 9 with the shield disposed in an unreleasible state.

Once a medical procedure is finished and it is determined that device 510 should be disposed of, a firm distal force may be applied against button 640 to displace latch leg 648 to be permanently latched in a catch provided by slot 678 as seen in FIG. 13.

Figure 17:
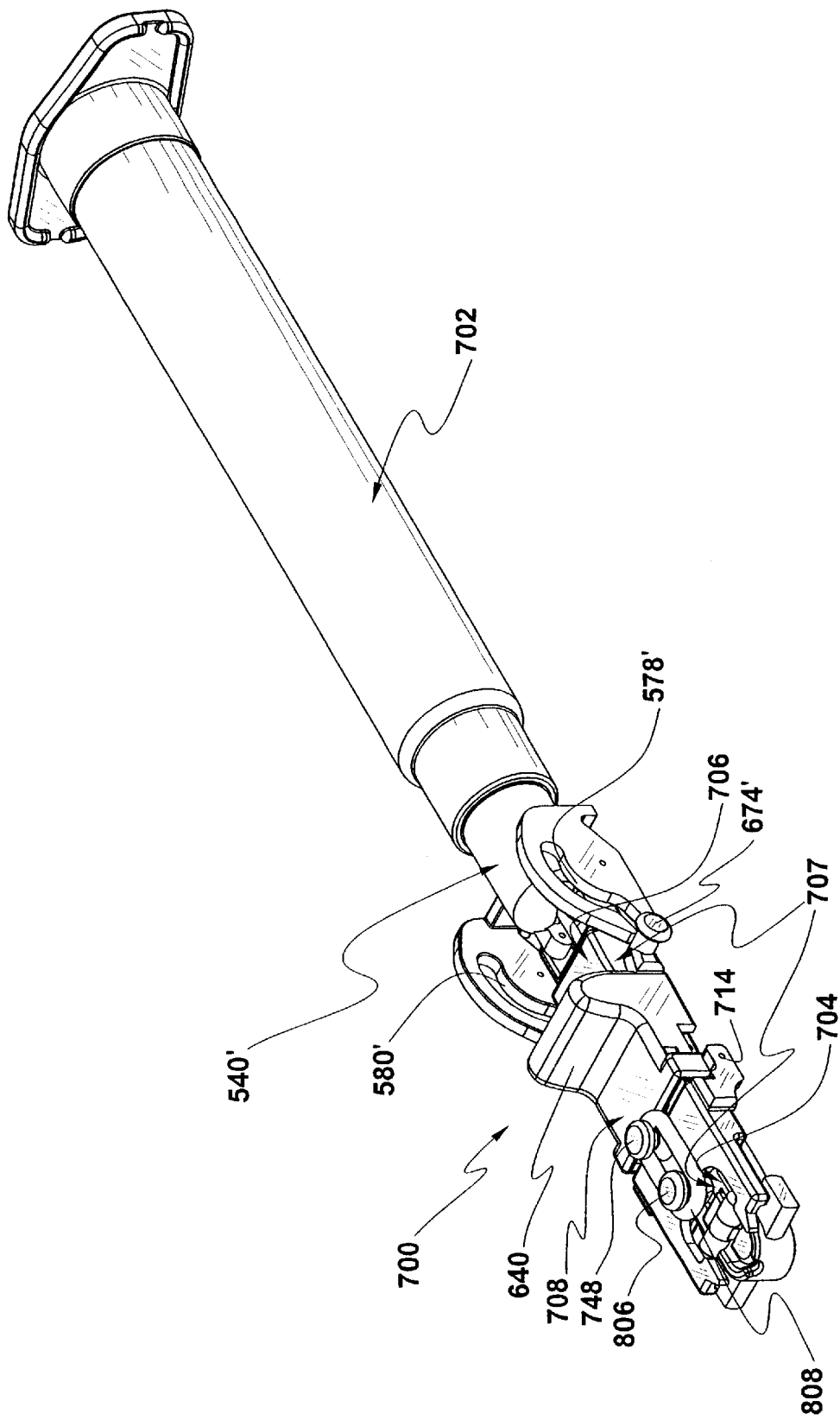
FIG. 17 is a perspective of another embodiment of a needle shield assembly which is affixed to a syringe.

Another device 700, seen in FIG. 17 affixed to a syringe barrel 702, also may be used to reaccess a medical needle without undue jeopardy of an inadvertent needle stick. Further, device 700 may be used with a connector or adapter (as disclosed in detail hereafter) to access fluid containment vessels, such as drug vials, vacuum sampling tubes, cord containers and "Y" injection sites, without accessibly exposing a needle tip (such as needle tip 100).

Figure 18:
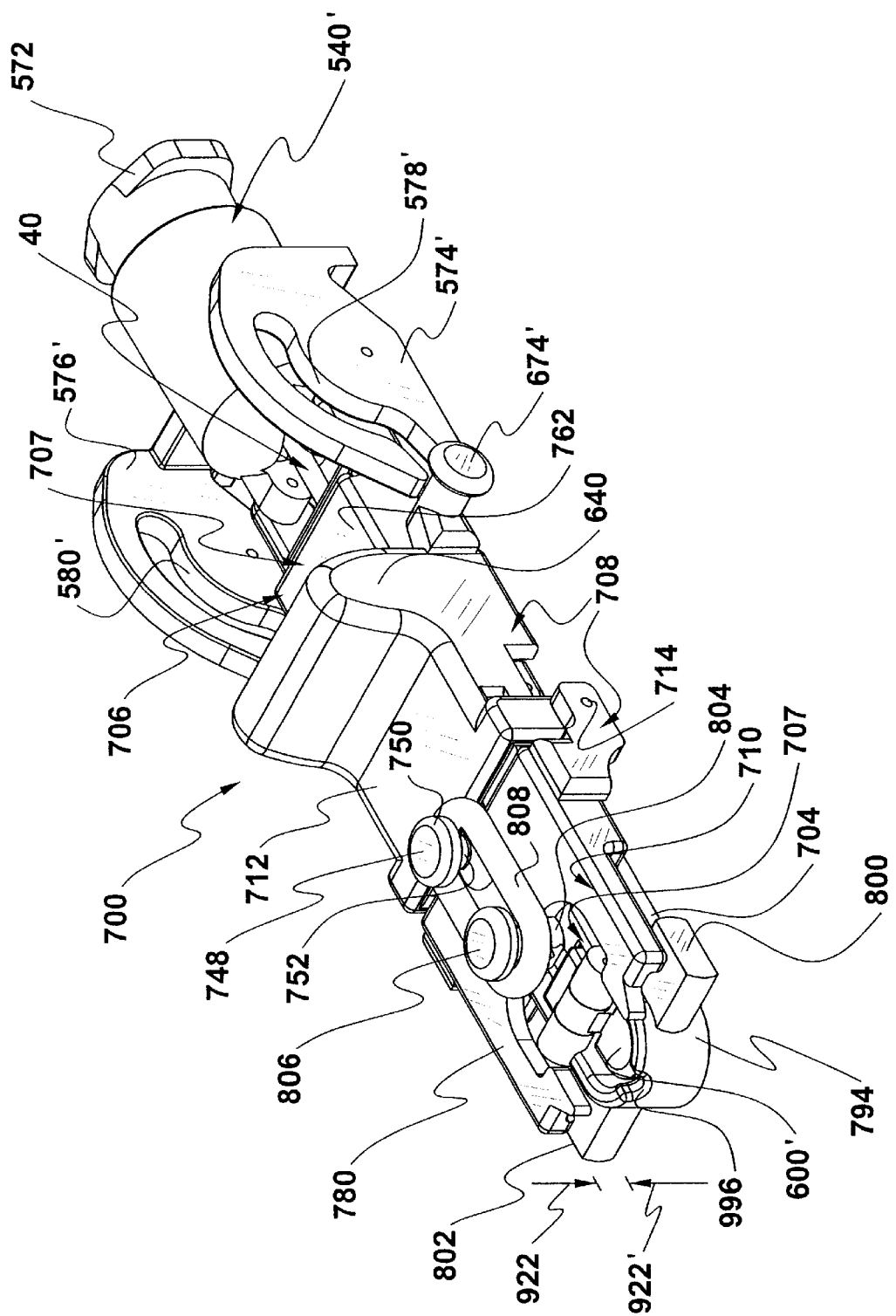
FIG. 18 is a perspective of a disconnected needle shield assembly of the embodiment seen in FIG. 17.

Device 700 is assembled from a distal section 704, a proximal section 706, a needle hub assembly 540' and a slider assembly 708. In combination, distal section 704 and proximal section 706 form a safety shield 707. A magnified representation of device 700 is seen in FIG. 18, wherein hub assembly 540' is seen to have a proximally disposed female luer lock fitting 572. Affixed to hub assembly 540' are two guides 574' and 576', which are similar in form and function to guides 574 and 576. Similar to guides 574 and 576, guides 574' and 576' have guide tracks 578' and 580'. A hollow medical needle 40 is securely affixed in hub assembly 540' by processes well understood in the art of syringe needle manufacture.

Similar to slider 550, slider assembly 708 has a pair of laterally affixed, juxtaposed knobs 674' and 676' (see FIG. 22) which are sized and disposed to be constrained to travel along guide tracks 578' and 580' as slider assembly 708 is proximally displaced. Different from slider 550, slider assembly 708 has a distal section 710 as well as a proximal section 712.

Proximal section 712 has a button 640', similar in form and function to button 640 (see FIGS. 9–12). Similar to an earlier disclosed button, button 640' may be used to displace slider assembly 708 proximally to fold distal segment 704 against proximal segment 706 to bare needle 40 for use and to displace slider assembly 708 distally to unfold segments 704 and 706 to protectively enclose needle 40.

A pair of hinges 714 and 716 (see FIG. 22 where slider assembly 708 is seen as a separate part) hingeably join proximal segment 712 to distal segment 710. It should be noted that hinges 714 and 716 may be living hinges when slider assembly 708 is injection molded. Slider assembly 708 may be injection molded using polypropylene as may hub assembly 540', distal segment 704 and proximal segment 706. Similar to slider assembly 708, moldable portions of hub assembly 540', distal segment 704 and proximal segment 706 may each be injection molded as a single part interconnected by living hinges for intersegment and hub to segment hinges which are disclosed in detail hereafter.

Proximal section 712 further comprises parallel exterior of sides 718 and 720 which extend, generally inferiorly, from a superiorly disposed button 640, to a pair of respective inwardly protruding slide rails 722 and 724, respectively. Distal from button 640, proximal segment 712 has a planar top piece 726.

Distal section 710 has a transverse, planar top piece 728 which lies in substantially the same plane as planar top piece 726 when distal section 710 and proximal section 712 are unfolded and aligned. Disposed at right angles to planar top piece 728 are a pair of juxtaposed sides 730 and 732, which extend from planar top piece 728 to form a respective pair of inwardly directed, bottom rails 734 and 736. Section 710 also has an arcuate opening 738, partially closed by a pair of inwardly disposed tongues 740 and 742. An inward surface 744 of opening 738 has a centrally disposed arcuate notch 746. Referring, again, to FIG. 18, distal section 710 has an upwardly protruding knob 748 having a large diameter superior portion 750 and an inferiorly disposed smaller diameter portion 752.

Figure 20:
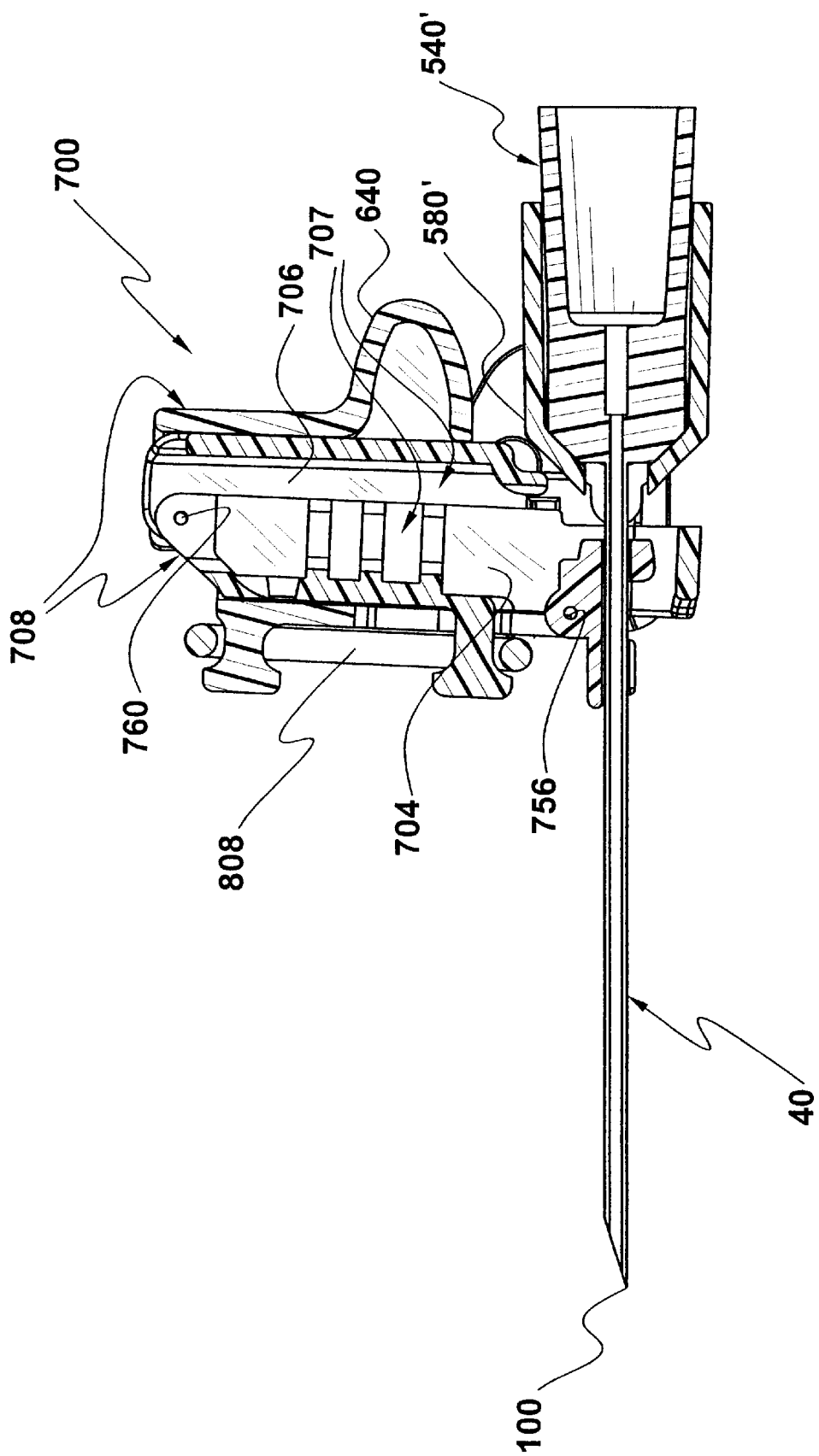
FIG. 20 is a cross section of the needle shield assembly seen in FIG. 18 with the assembly folded for access to an associated medical needle.
Figure 21:
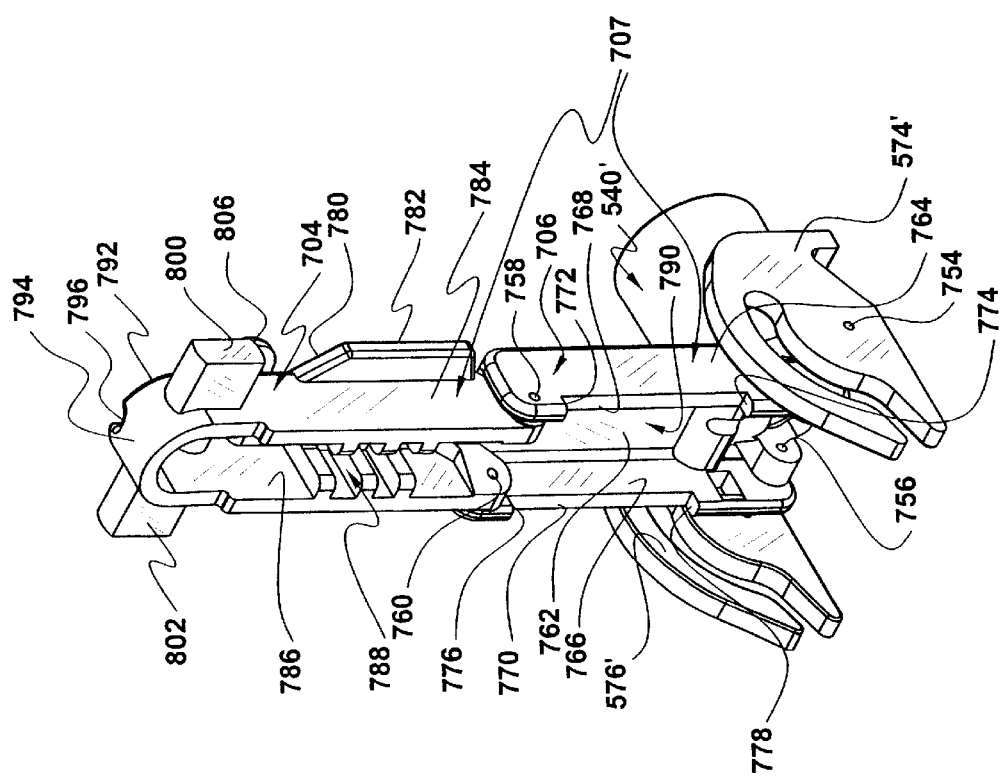
FIG. 21 is a perspective of a needle shield without the associated medical needle.

An "as may be molded" rendition of a combined hub assembly 540' (without luer lock fitting 572), distal segment 704 and proximal segment 706 is seen in FIG. 21. Note that proximal segment 706 is hingedly affixed to each guide 574' and 576' by a respective hinge 754 and 756, which permits proximal segment 706 to rotate to an orthogonal state relative to hub assembly 540', as seen in FIG. 21, and to an extended state along the long axis of needle 40 as seen in FIG. 18. Similarly, distal section 704 is hingedly affixed to section 706 by respective hinges 758 and 760, permitting section 704 to be aligned with section 706 as seen in FIGS. 18 and 21 and to be folded to bare needle 40 as seen in FIG. 20.

Proximal segment 706 has a substantially planar top surface 762, as may be seen on each side in FIGS. 18 and 21. Distending downward orthogonally from top surface 762 are a pair of substantially parallel sides 764 and 766, best seen in FIG. 21. At the bottom of each side 764 and 766 is a linear indentation 768 and 770, respectively. Indentation 768 is bounded by a distal stop 772 and a proximal stop 774. Similarly, indentation 770 is bounded by a distal stop 776 and a proximal stop 778. Purpose and function of stops 772, 774, 776 and 778 is disclosed in detail hereafter.

Distal segment 704 also has a substantially planar top 780 and a pair of juxtaposed wings which extend laterally outward, one wing 782 is seen in FIG. 21. The other wing, referenced herein as 782', is not shown but is a mirror image of wing 782. Distal segment 704 has a pair of juxtaposed side members 784 and 786 orthogonally connected to top 780. Each side member has a plurality of downwardly distending ribs which are separated to form a channel 788 for a needle 40. Similarly, sides 764 and 766 are likewise separated to provide a similar channel 790 which is continuous with channel 788 when segment 704 is aligned with segment 706.

At a distal site 792, segment 704 has a closed end 794. Closed end 794 may have a notch 796 which provides a clear pathway whereby a needle tip 100 being constrained outward from site 792 may clear and not touch any part of segment 704. Also disposed proximal to closed end 794 are a pair of juxtaposed substantially rectangular members 800 and 802, the purpose and function of which is disclosed in detail hereafter. Superiorly disposed on top 780 is a stem 804 (see FIG. 18) which culminates in a bulbous knob 806. Note that center points of stem 804 and portion 752 lie in a line which is aligned with the long axis of needle 40.

Figure 23:
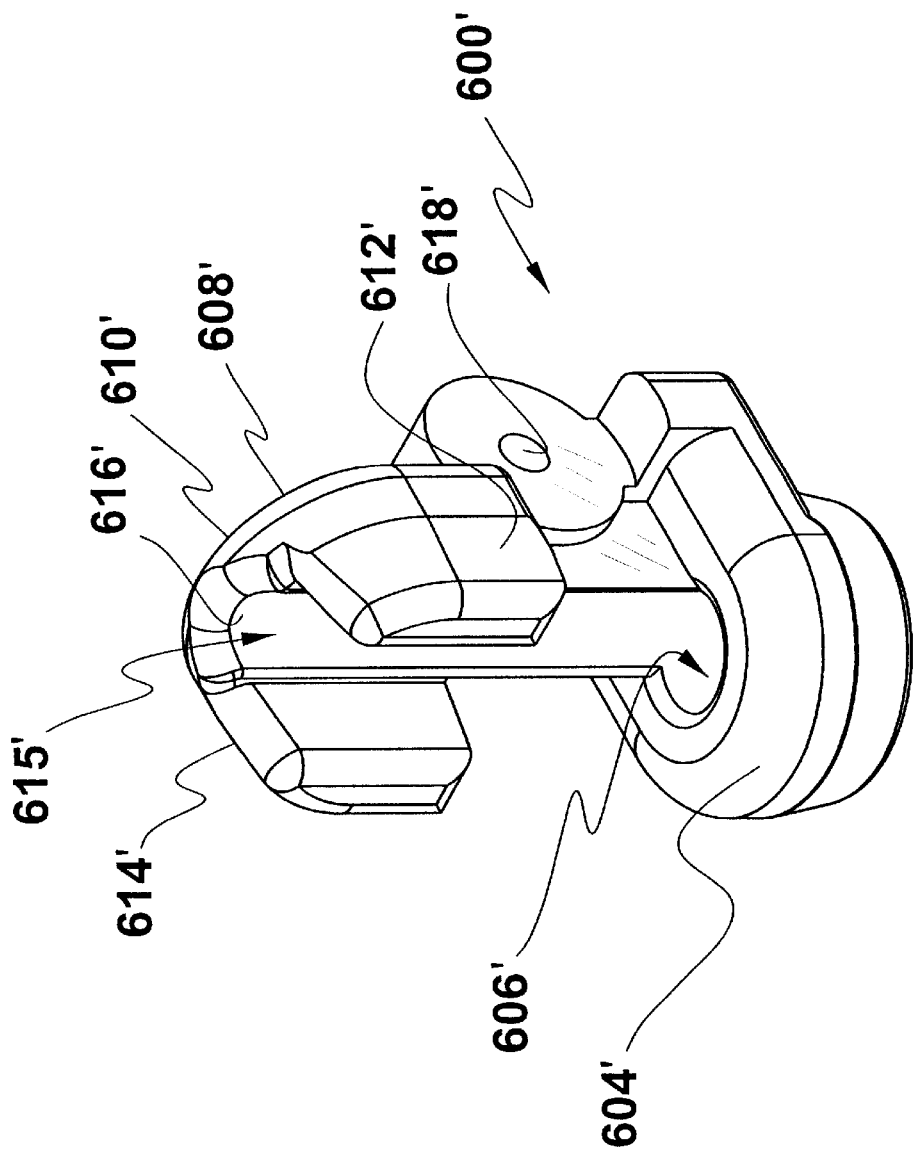
FIG. 23 is a perspective of a needle guide associated with a distal segment of the needle shield.

Similar to guide 600 of arm 582, earlier disclosed, segment 704 has a needle guide 600' affixed thereto as seen in FIG. 18. Needle guide 600' is seen in FIG. 23 as a separate part for clarity of presentation, however, it is preferred that guide 600' be integrally molded with distal segment 704. Guide 600' has a proximally disposed guide ring 604' which has a medially disposed through hole 606' which is sized for facile passage of a needle 40 (not shown in FIG. 23). Note that ring 604' should be disposed geometrically to constrain and guide needle 40, as segments 704 and 706 are folded to bare needle 40, in such a manner that tip 100 does not touch any part of segment 704, especially closed end 794. In this manner, tip 100, which may be fragile and prone to being damaged, is guided to move past end 794 without being damaged or contaminated. Needle guide 600' also has a distally disposed shroud 608', having a cover part 610' and a pair of side protectors 612' and 614'. Note that side protectors 612' and 614' and cover part 610' define an inner surface 615' and an opening 616' through which needle 40 glides as segments 704 and 706 are folded and unfolded. Needle guide 600', when formed as a separate part, has a transverse through hole 618' disposed for use in hinge 602', best seen in FIGS. 25, 28 and 30. It should be specially noted that care should be taken in defining the position for hinge 602'. As will become evident from disclosure provided hereafter, it is critical that hinge 602' be situated to permit rotation of segment 704 about needle 40 in such a manner, as segment 704 is folded, that members 800 and 802 (seen in FIG. 24) are in continuous alignment with the long axis of needle 40.

Referring once more to FIG. 18, residing about stem 804 and portion 752 of knob 748 is an energy storing elastic ring 808 used to store energy as slider assembly 708 is displaced proximally relative to shield 707. However, as seen in FIG. 18, ring 808 is unstressed and remains so until slider assembly 708 is displaced proximally in the process of baring needle tip 100. Ring 808 should be made from an elastic which has sufficient resiliency to displace slider assembly 708 distally to engage temporary latches as disclosed hereafter. Ring 808 is constrained to remain affixed to stem 804 and portion 752 by top 780 and knobs 748 and 806. It is important to note that any energy storing member such as a metal or plastic spring or other element which would be stressed as slider assembly 708 is displaced proximally and which would have sufficient resiliency to return slider assembly 708 to the state seen in FIG. 18 may be used within the scope of the invention.

Figure 19:
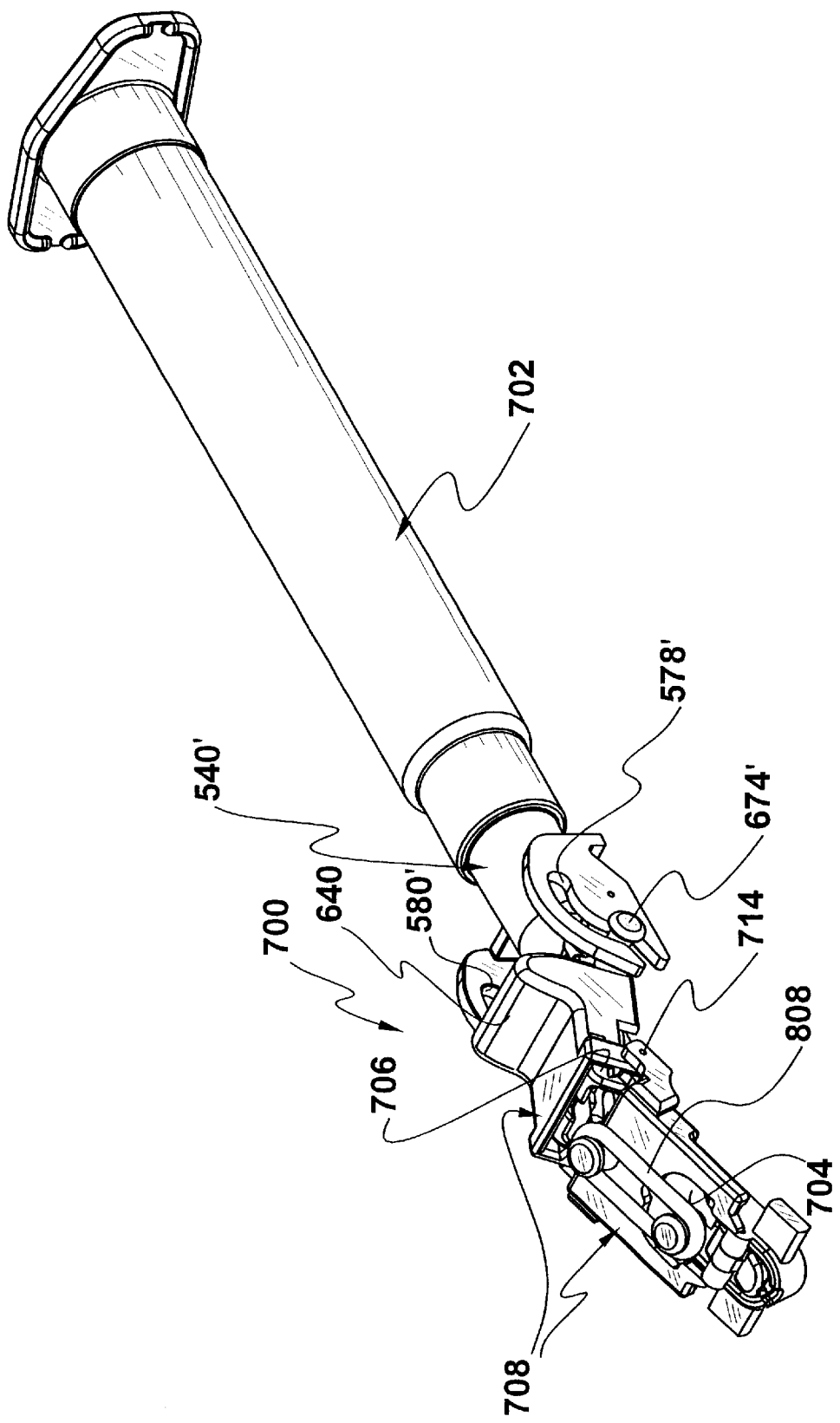
FIG. 19 is a perspective of the embodiment of FIG. 17 with the needle shield assembly partially folded.

As seen in seriatim in FIGS. 17, 19 and 20, displacing slider assembly 707 proximally causes slider assembly 708 and distal segment 704 and proximal segment 706 to fold from an extended state seen in FIG. 17 through an intermediate state depicted in FIG. 19 to a folded state seen in FIG. 20. It should be understood that, when in the extended state of FIG. 17, shield 707 is securely, but releasibly, latched for safety.

Reference is again made to FIG. 22 where releasible latching members are best seen. Along a line in the same plane as bottom rail 736 is a more proximal rail 810 disposed along side 720 of proximal section 712. A similar rail 812 (hidden in FIG. 22) is similarly disposed along side 718 of proximal section 712. During assembly, bottom rails 734 and 736 of slider assembly 708 are slideably engaged about wings 782 and 782', respectively. Each wing (such as wing 782 seen in FIG. 21) forms a catch for a latch formed by one rail of rails 810 and 812.

Further, when slider assembly 708 is slideably joined to shield 707, sides 718 and 720 are disposed about sides 764 and 766 of proximal segment 712 such that rails 722 and 724 slide upon linear indentations 768 and 770, respectively. So joining of slider assembly 708 to proximal segment 712 is facilitated by using a flexible resilient material such as polypropylene for slider assembly 708 and by providing beveled edges 814 and 816 for rails 722 and 724, respectively, which permit slider assembly 708 to "snap" into engagement with proximal segment 712. So engaged, rails 722 and 724 are constrained to slide proximally and distally between stops 774 and 778 and 768 and 776, respectively, and are so limited by the stops.

When shield 707 and slider assembly 708 are disposed as seen in FIG. 17, rails 810 and 812 are engaged with wings 782' and 782, respectively. This engagement deters action of all hinges 758, 760, 714 or 716. It is not until slider assembly 708 is displaced proximally, such as under forces placed upon button 640, that such latches are disengaged from the catches and hinges 758, 760, 714 and 716 are free to rotate. By this same action, elastic ring 808 is stressed and energy is resultingly stored therein. Note, at this point hinges 758 and 714 and 760 and 716 should be transversely aligned relative to the long axis of needle 40. Also, concurrent with release of the hinges, latches and catches, stems of knobs 674' and 676' are displaced into tracks 578' and 580', respectively to urge hinges 758, 760, 714 and 716 to lift upward from needle 40 and thereby fold shield 707 along with slider assembly 708, as seen in FIGS. 19 and 20. Note that slider assembly 708 and shield 707 are shown in cross section, magnified and without connection to a syringe for clarity of detail in FIG. 20.

Reversing forces upon button 640 unfolds shield 707 and slider assembly 708 about needle 40. Once shield 707 and slider assembly 708 are unfolded, retraction of elastic ring 808 reengages rails 810 and 812 against the wings and shield 707 and slider assembly 708 are once more releasibly latched. A permanent latch may be achieved in the manner disclosed in FIGS. 9–13, as one skilled in the art of plastics design would understand.

By so being able to efficaciously cover and reaccess a medical needle, a plurality of medical procedures, separated by time and distance, may be performed using the same needle with safety not possible when a single use safety needle is employed. However, there are a number of common medical procedures which require a needle insertion which too often provide an opportunity for an inadvertent needle stick. Such is the case when a syringe has been used to draw blood from a patient and the blood is transferred to a vacuum sample tube for analysis. In this case, an often contaminated needle, after removal from a patient, is driven through a stopper of the vacuum sample tube without benefit of any safety mechanism.

Similarly, when syringes are filled from drug vials, a needle is bared to pierce a membrane on the vial before using contents of the syringe in a medical procedure. As it is against standard precautions to recap a needle, the needle may be transported to a patient site uncovered.

Another example of a case where needle sticks have been of concern in the past has been at "Y" connectors on intravenous (IV) injection sites. For purposes such as this, "needleless systems" have, in many instances, replaced needles. However, this has not been achieved without cost. History has shown these alternative needleless systems to be much more expensive than needles, alone.

Of course, direct percutaneous entry into a patient is likely the most significant opportunity for inadvertent sticks by a contaminated needle. It should be recognized that every time a needle is bared for use in a medical procedure, there is opportunity for contamination which endangers either a health care worker or patient. These needs have motivated the broadened use and applications of device 700 as disclosed hereafter.

Reference is now made to FIGS. 24–34 wherein methods and apparatus related to passively activating safety connectors or adapters for syringes are disclosed. Note in FIG. 24 that device 700 affixed to a syringe 702 is seen in association with a vial 900 and vial adapter 902. Vial 900 may be any general vial from which fluids are drawn into a syringe or where syringe contents are injected from a syringe into a vial (e.g. blood culture bottles). Most often vial 900 would be considered to be a vial from which drugs are drawn for hypodermic delivery to a patient.

Figure 26:
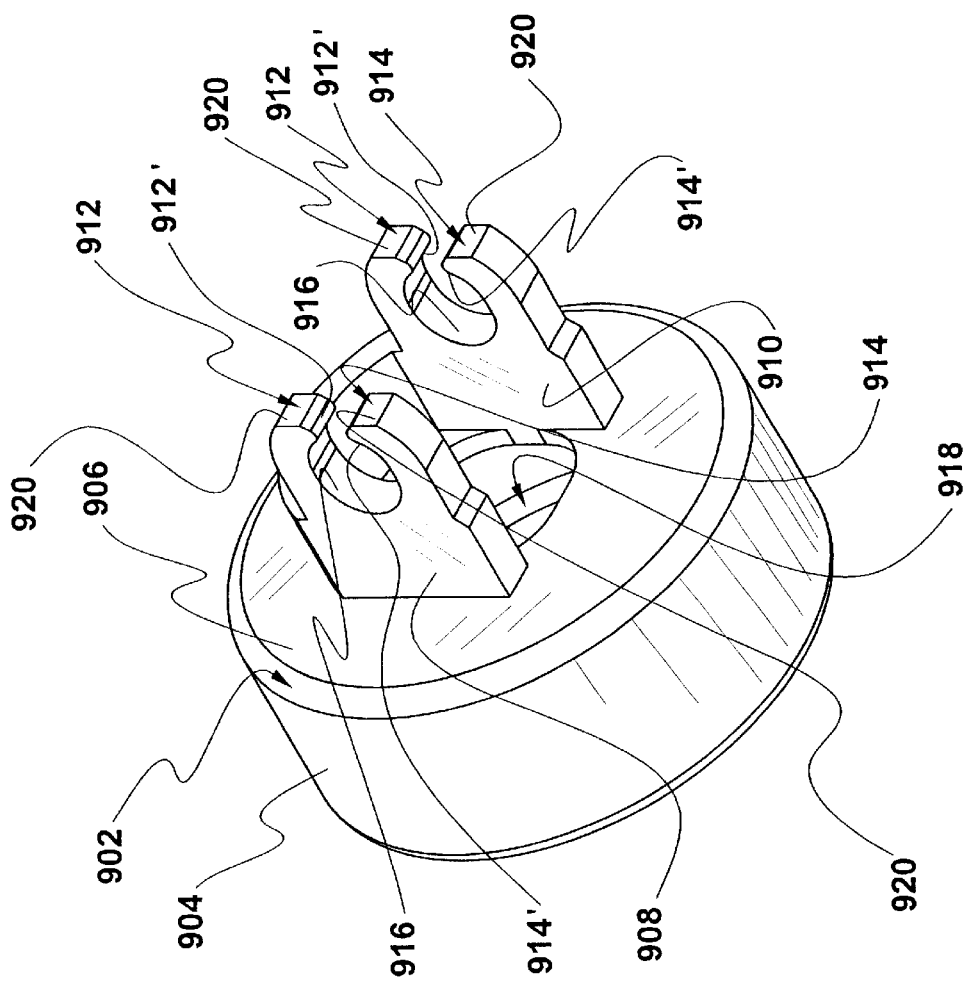
FIG. 26 is a perspective of a connector adapter associated with the needle shield assembly and seen in FIG. 24.
Figure 27:
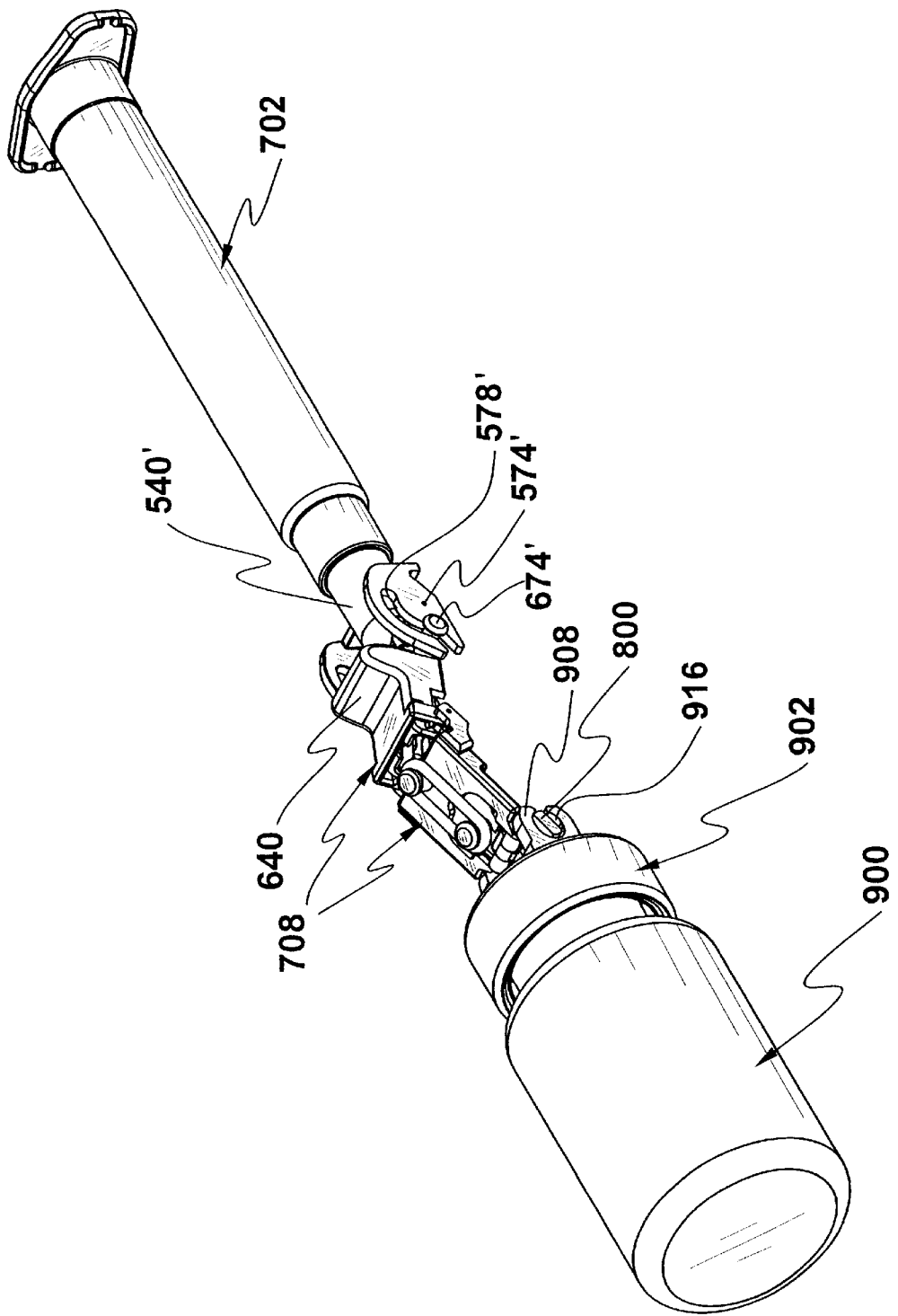
FIG. 27 is a perspective of the vial and connector adapter of FIG. 24 disposed in communication with the needle shield assembly and resulting flexure (folding) of the needle shield assembly.

Adapter 902 is a connector between vial 900 and device 700 which provides, first, an interface to a keying actuator by which a latch is released to be permitted to fold and, second, a tool by which shield 707 is selectively folded away from needle tip 100. As best seen in FIG. 26, adapter 902 has a snap or attachment ring 904 by which adapter 902 is securely affixed to vial 900 and a substantially planar face 906 which is disposed over a pierceable access membrane through which fluids are commonly drawn into a syringe via a syringe needle 40.

Jutting outward from face 906 are a pair of connecting members 908 and 910. Each connecting member 908 and 910 has a pair of outwardly projecting prongs 912 and 914 which define a hollow cavity 916. Though other geometries may be used within the scope of the invention, each cavity 916 is substantially circular in cross section. Disposed between prongs 912 and 914 is a vial access orifice 918 where through a needle tip 100 and needle 40 passes to pierce a pierceable membrane of vial 902. Further, each prong 912 and 914 ends abruptly with a flat surface 920, the purpose for which is disclosed in detail hereafter. Adapters such as adapter 902 may be made from polypropylene or other material which has sufficient rigidity to act as a connector which may be used interactively with shield 707 and which has sufficient resiliency for use as a plastic connector.

Each prong pair 912 and 914 has an inwardly disposed pair of curved surfaces 912' and 914', respectively, which are separated by a predetermined distance. Referring once more to FIG. 18, member 802 has a predetermined cross sectional width delineated by arrows 922 and 922'. Member 800 has a similar predetermined cross sectional width. As may be seen in combination in FIGS. 24 and 27, to selectively acquire protected access to needle tip 100 through the use of adapter 902, prong pairs 912 and 914 (see FIG. 26) are displaced until members 800 and 802 completely pass by associated prong curved surfaces 912' and 914'. Note that the minimum predetermined distance separating each curved surface 912' and 914' should be somewhat less than the cross sectional widths of members 800 and 802. Even so, resiliency of prong pairs must be sufficient to allow each member 800 and 802 to pass into an associated cavity 916 without undue force.

Figure 22:
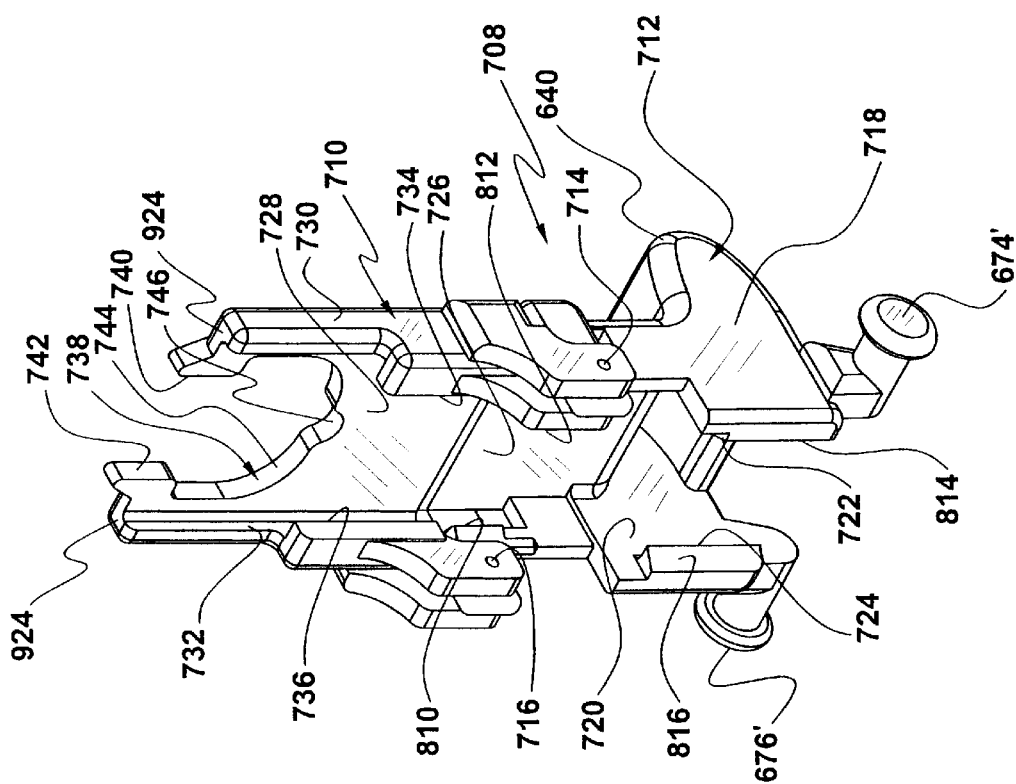
FIG. 22 is a perspective of a slider portion of the needle shield assembly of FIG. 18.

Referring to FIG. 22, it may be noted that each tongue 740 and 742 has a flat distally disposed surface 924 which is sized and positioned to impact a surface 920 as adapter 902 is connected about members 800 and 802. The act of making such a connection displaces tongues 740 and 742 and resultingly proximally displaces slider 708. In this manner, each set of prongs 912 and 914 act as keys which displace tongues 740 and 742 (which are protected from displacement by members 800 and 802, respectively), thereby effecting a selective release of the latching interface between slider 708 and shield 707. Just as proximally displacing button 640 causes slider 708 to release latches from catches and permits shield 707 to fold from a needle protecting state to a needle 40 access state, connection adapter 902 to members 800 and 802 results in the same action through tongues 740 and 742.

One of the critical factors of delivering needle 40 into a membrane via an adapter or connector such as adapter 902 is that no undue stress resulting from forces which are not in line with the long axis of needle 40 should be placed upon needle 40 either when needle travel is distal or proximal. To accomplish this, members 800 and 802 must be disposed along a transverse line of rotation of distal segment 704 of shield 707 about the long axis of needle 40. This line of rotation is determined, in combination, by axis of rotation of hinge 602' and deployment of hole 606' of needle guide 600' (see FIG. 28). Proper deployment assures that no undue torquing or bending force is placed upon needle 40. This is especially critical when small diameter needles are used.

Figure 24:
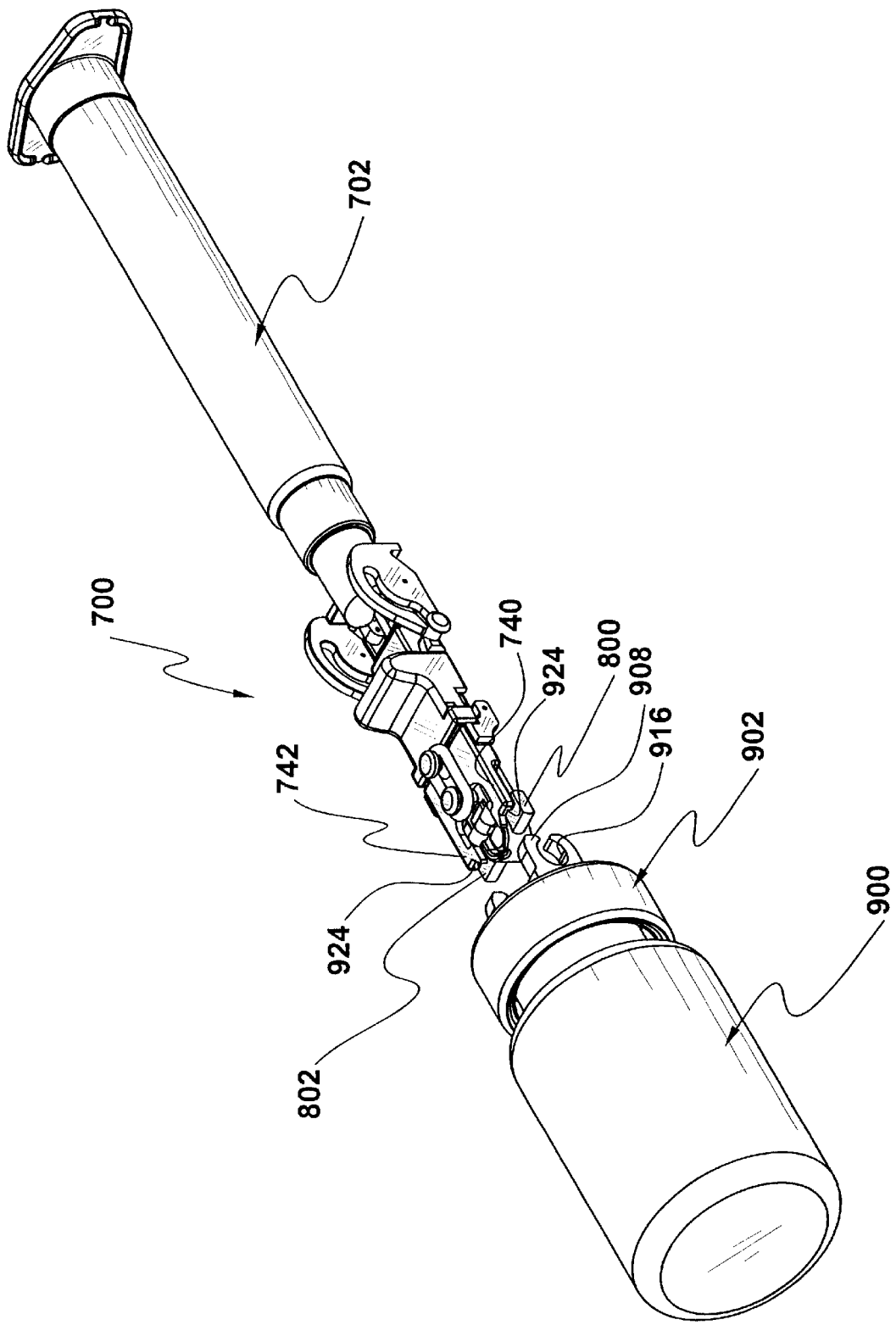
FIG. 24 is a perspective of the embodiment of FIG. 17 and a drug vial having a connector adapter affixed thereto.
Figure 25:
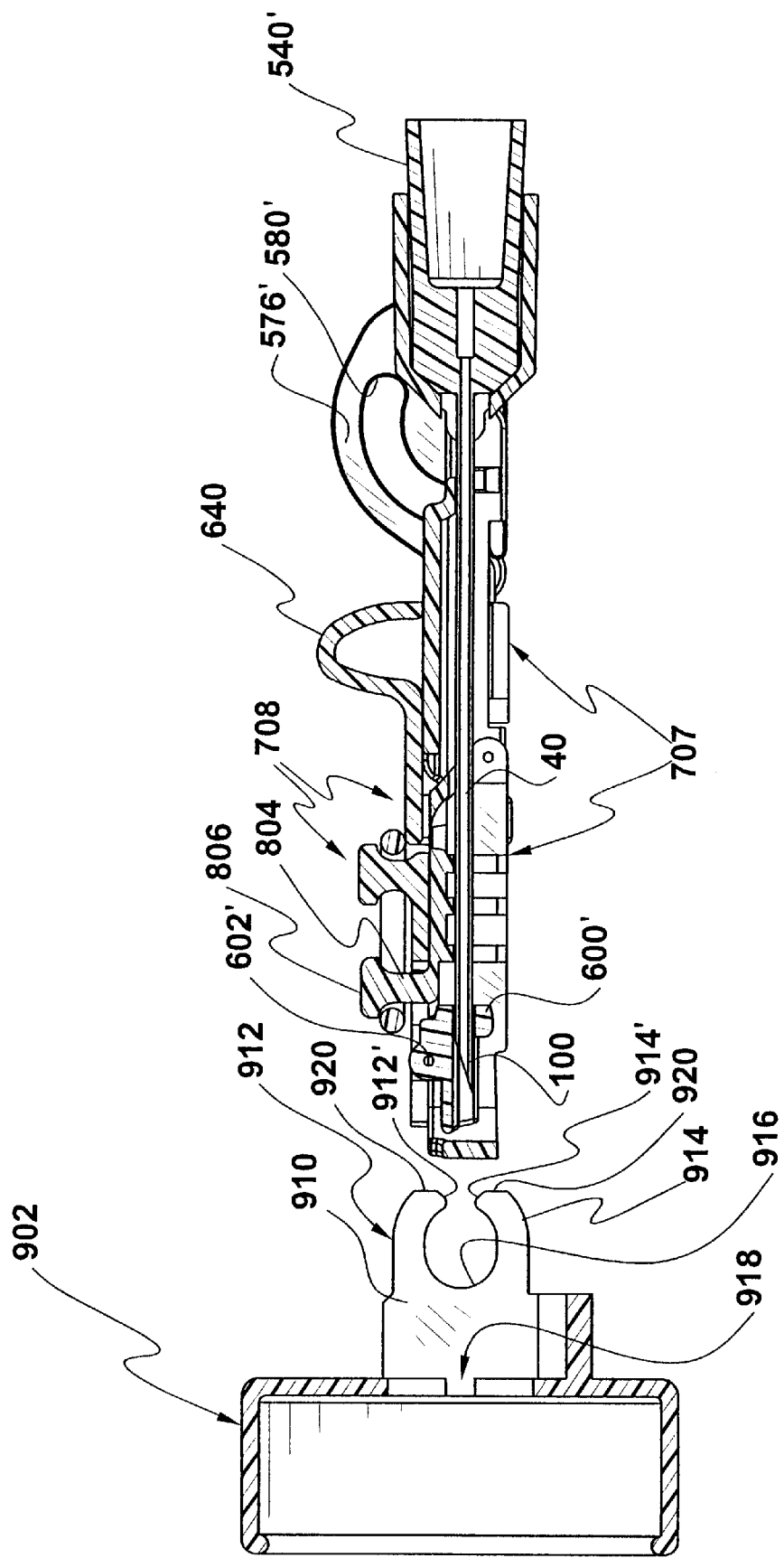
FIG. 25 is a cross section of the perspective seen in FIG. 24.

Passive operation is defined to be operation which requires no additional steps other than those usually employed to operate a device. Note that needle access is provided with shield 707 and adapter 902 operating jointly to provide access by needle 40 into vial 900 without additional steps. As seen in FIG. 24, adapter 902, previously affixed to vial 900, is displaced toward needle tip 100 (hidden in FIG. 24, but clearly seen with needle tip 100 untouched by needle guide 600' in FIG. 25) in a manner similar to displacement of a standard vial toward any needle tip affixed to a syringe. Displacement of prongs 912 and 914 about members 800 and 802 causes displacement of slider 708 and ultimate rotation of shield 707, see FIG. 27. Note, in FIG. 27, that rotation of shield 707 causes similar rotation of members 800 and 802 relative to prongs 912 and 914 resulting in capture of each member 800 and 802 (not seen in FIG. 27) within an associated cavity 916. Members 800 and 802 are affixed and so captured until shield 707 is once more completely unfolded (extended to a needle protected state).

Figure 28:
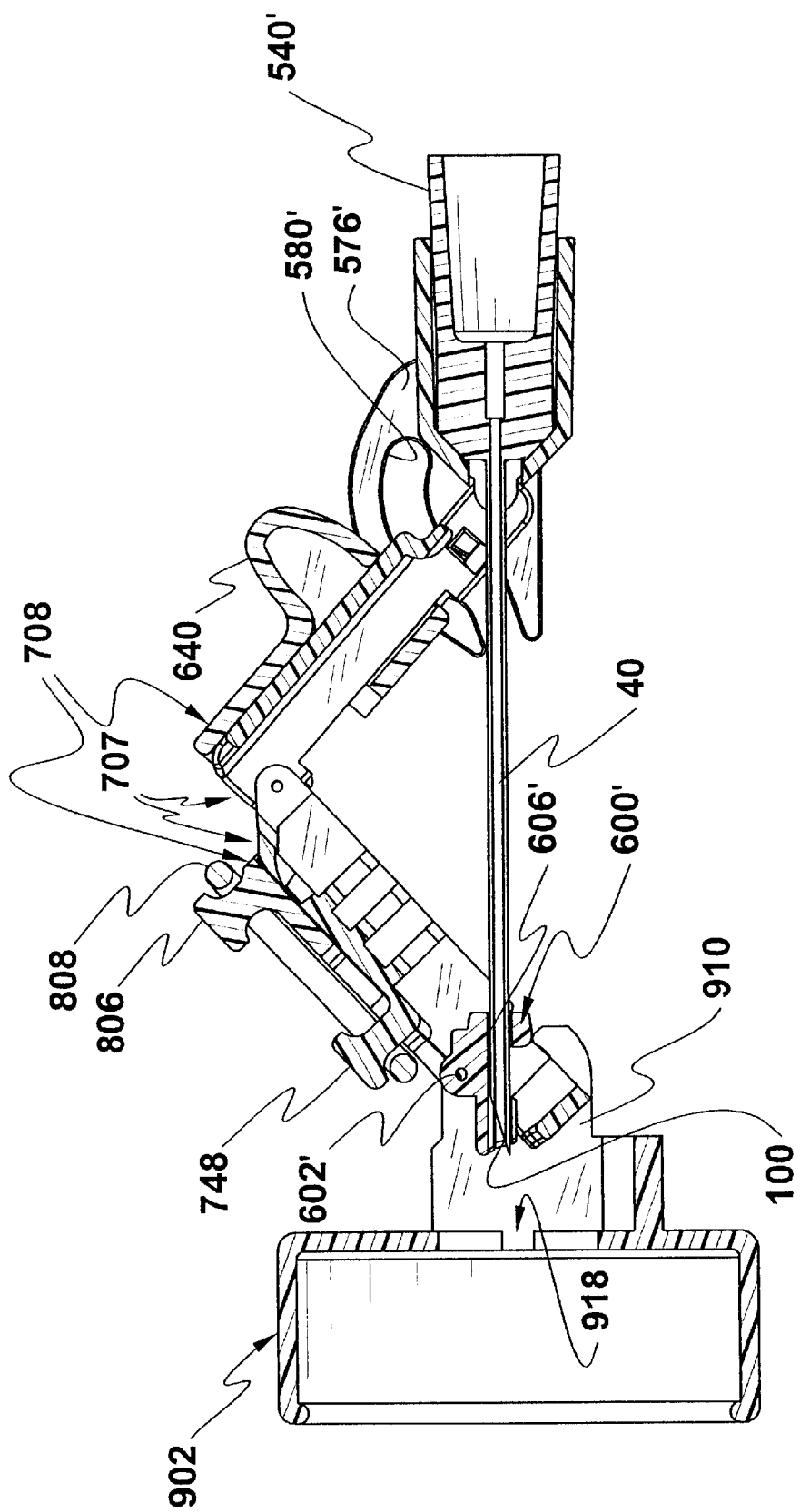
FIG. 28 is a cross section of the interconnected vial, connector adapter and needle shield assembly.
Figure 29:
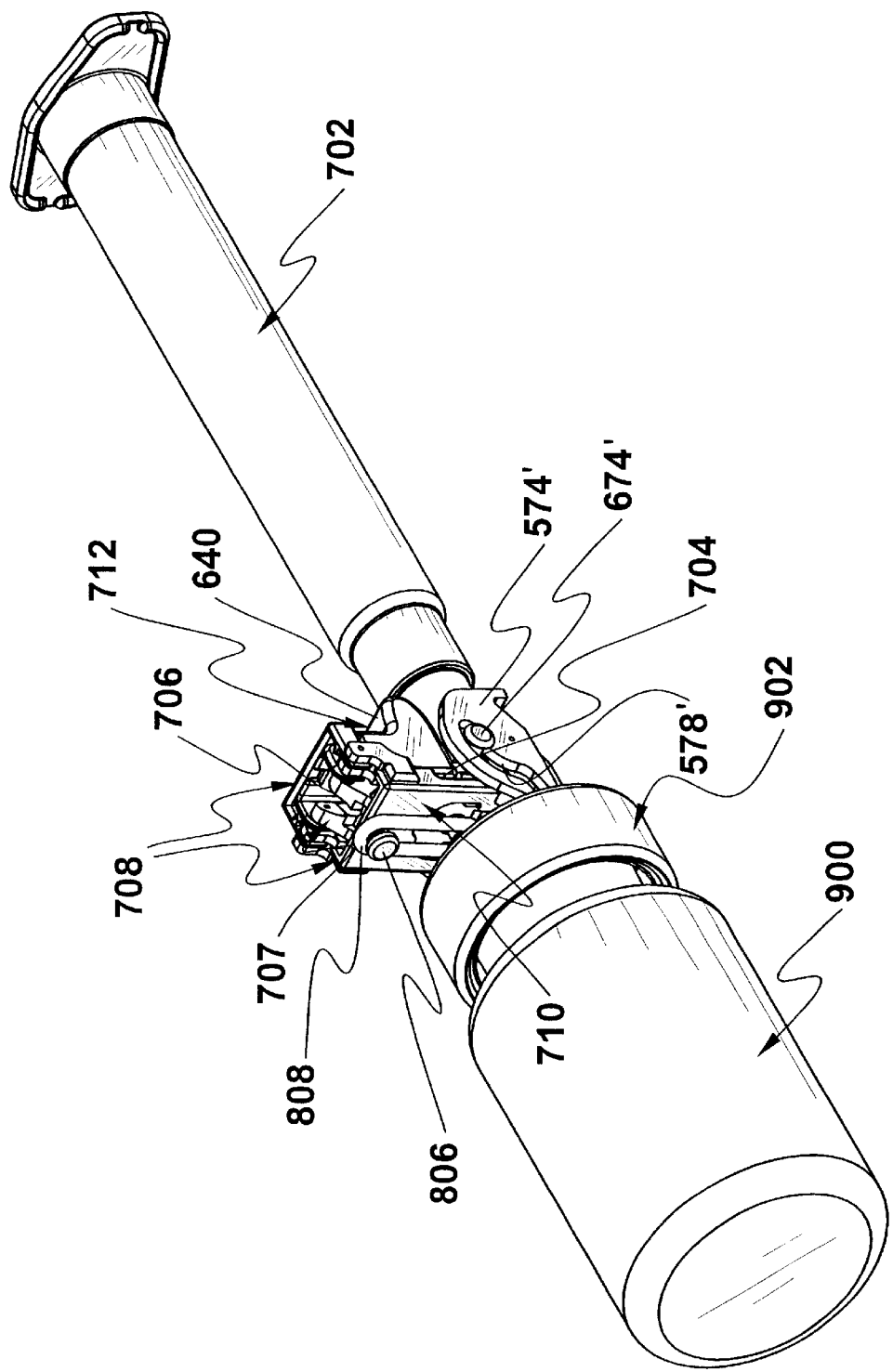
FIG. 29 is a perspective of the connector adapter engaging and folding the needle shield assembly.
Figure 30:
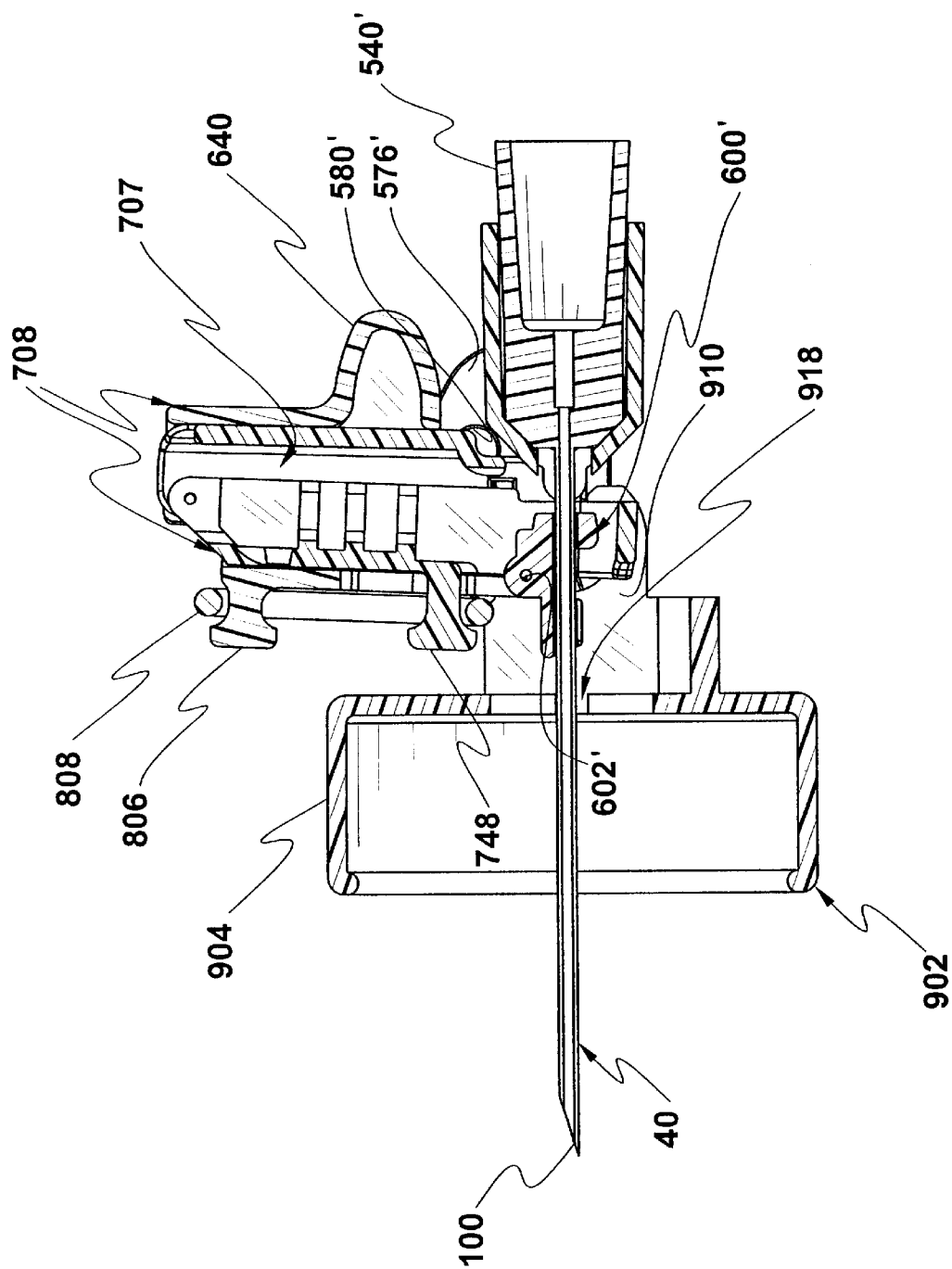
FIG. 30 is a cross section of the connector and needle shield assembly seen in FIG. 29 with the vial removed for clarity of presentation.
Figure 31:
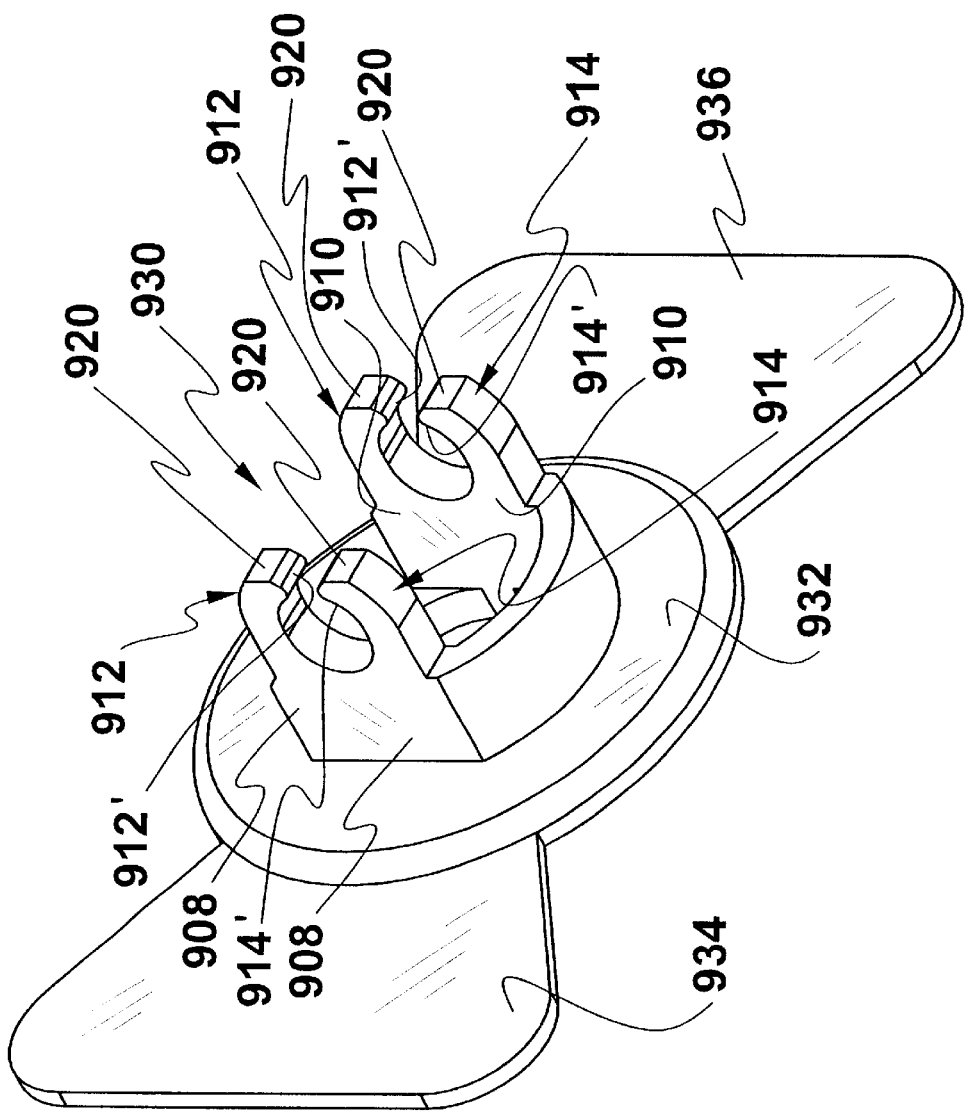
FIG. 31 is a perspective of an adapter for use in hypodermic applications.

Further, proximal displacement of adapter 902 toward needle hub assembly 540 causes needle guide 600' to urge needle tip 100 and needle 40 away from shield 707, as seen in FIG. 28. Continued displacement directs needle tip 100 through access orifice 918 and into vial 900 as seen in FIG. 29. A fully folded shield 707, with adapter 902 in place, is seen in FIG. 30.

As earlier mentioned, there are many opportunities to protect a needle where it is currently common practice to use a bare needle. The most common opportunity may be found in hypodermic applications. Today, there are no passive syringe needle protective devices, known to the inventors, for hypodermic needle procedures. By applying a connective element, similar to adapter 900, to a flat plate device, such as device 930, seen in FIG. 31, passive needle protection can be provided in hypodermic procedures as well. Note that device 930 has a flat plate 932 designed to provide an interface with skin. Similar to adapter 902, plate 932 has a pair of outwardly jutting connecting members 908 and 910. Rather than a attachment ring 904 of adapter 902, device 930 has a pair of wings 934 and 936 used to hold device 930 against skin as needle 40 is withdrawn at the end of a hypodermic procedure. As is the case of adapter 902, device 930 may be made from polypropylene, preferably by injection molding.

Connectors or adapters, similar to adapter 902 may be used for various other needle protecting applications. Examples of such applications are seen in FIGS. 32–35.

Figure 32:
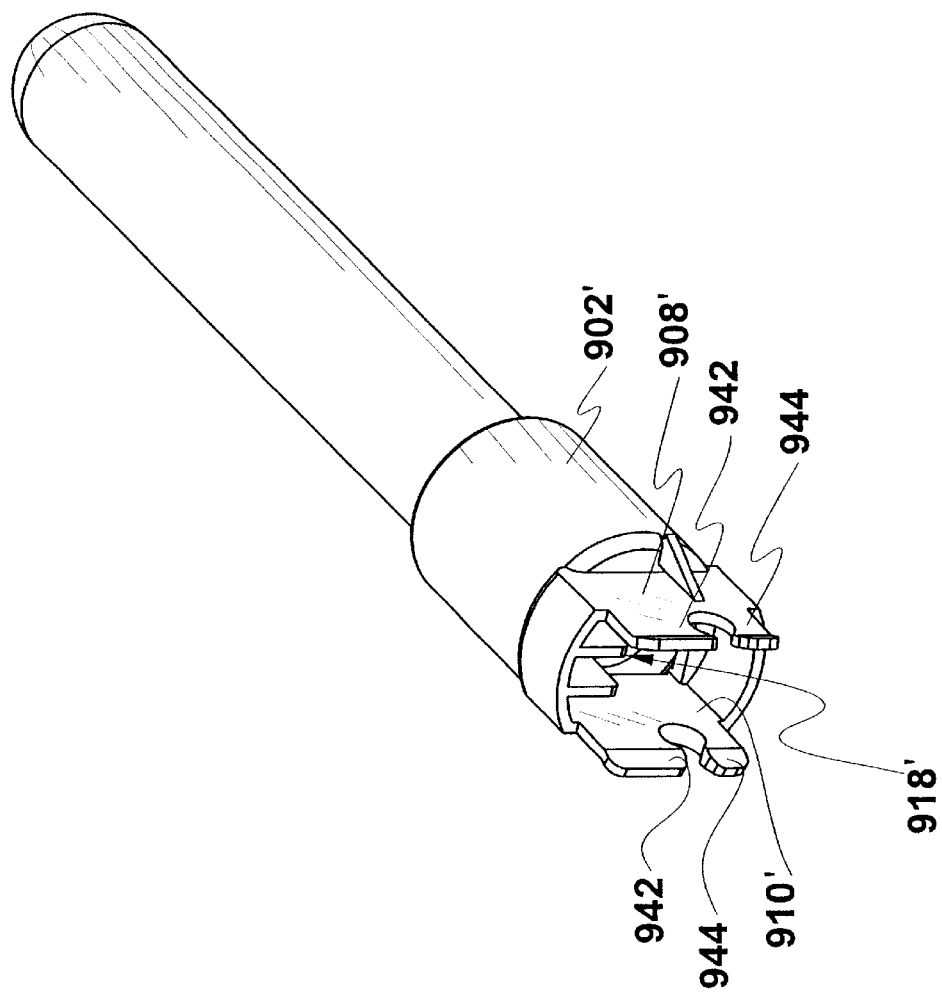
FIG. 32 is a perspective of a connector affixed to a vacuum sampling tube.

FIG. 32 shows a connecting adapter 902' affixed to a vacuum sampling tube 940. Adapter 902' has a pair of outwardly jutting connecting members 908' and 910' which are similar in form and function to connecting members 908 and 910 (see FIG. 26). An access orifice 918' (similar to orifice 918) provides a passageway for needle tip 100 and needle 40 to traverse to pierce a stopper of vacuum sampling tube 940. Prongs 942 and 944 provide an interface to device 700 which is equivalent to the interface provided by prongs 912 and 914 (see FIGS. 24–30).

Figure 33:
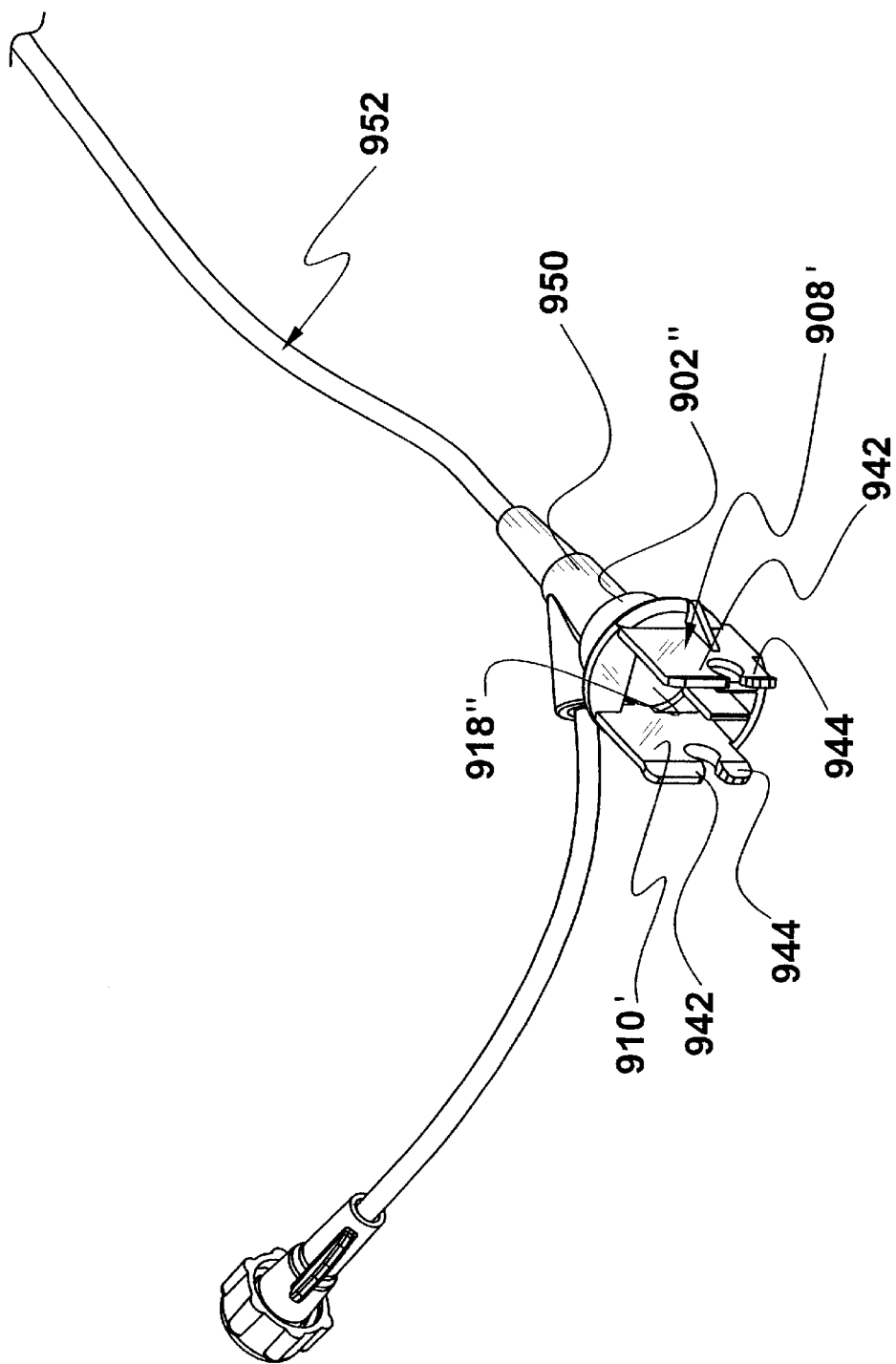
FIG. 33 is a perspective of a connector affixed to a "Y" injection site.

FIG. 33 shows a connecting adapter 902" affixed to a "Y" injection site 950 of an IV set 952. Adapter 902" has a pair of outwardly jutting connecting members 908' and 910' which are similar in form and function to connecting members 908 and 910 (see FIG. 26). An access orifice 918" (similar to orifice 918') provides a passageway for needle tip 100 and needle 40 to traverse to pierce a membrane of "Y" injection site 950. As is the case in the apparatus seen in FIG. 32, prongs 942 and 944 provide an interface to device 700 which is equivalent to the interface provided by prongs 912 and 914 (see FIGS. 24–30).

Figure 34:
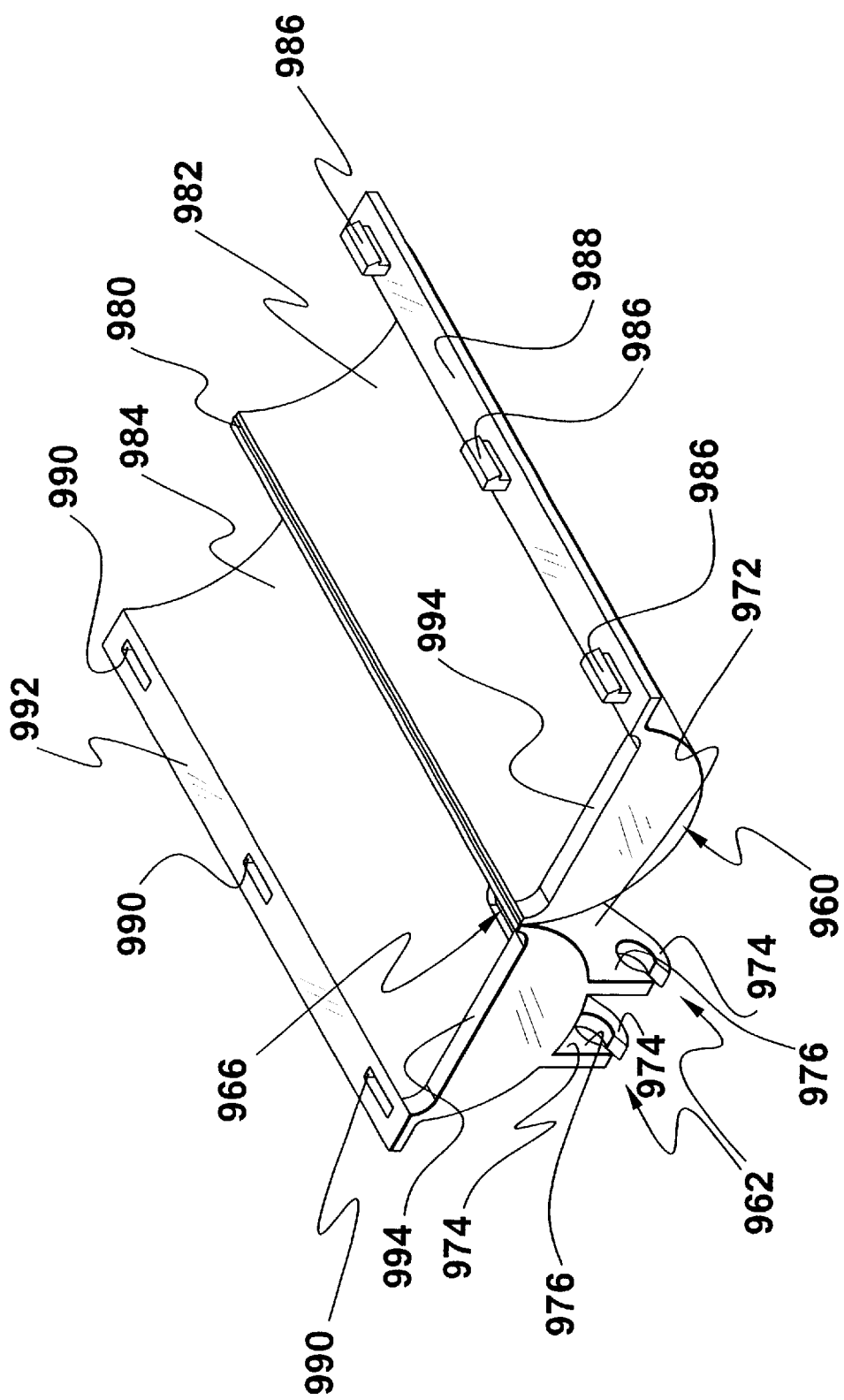
FIG. 34 is a perspective of an open umbilical cord container with an adapter affixed thereto.
Figure 35:
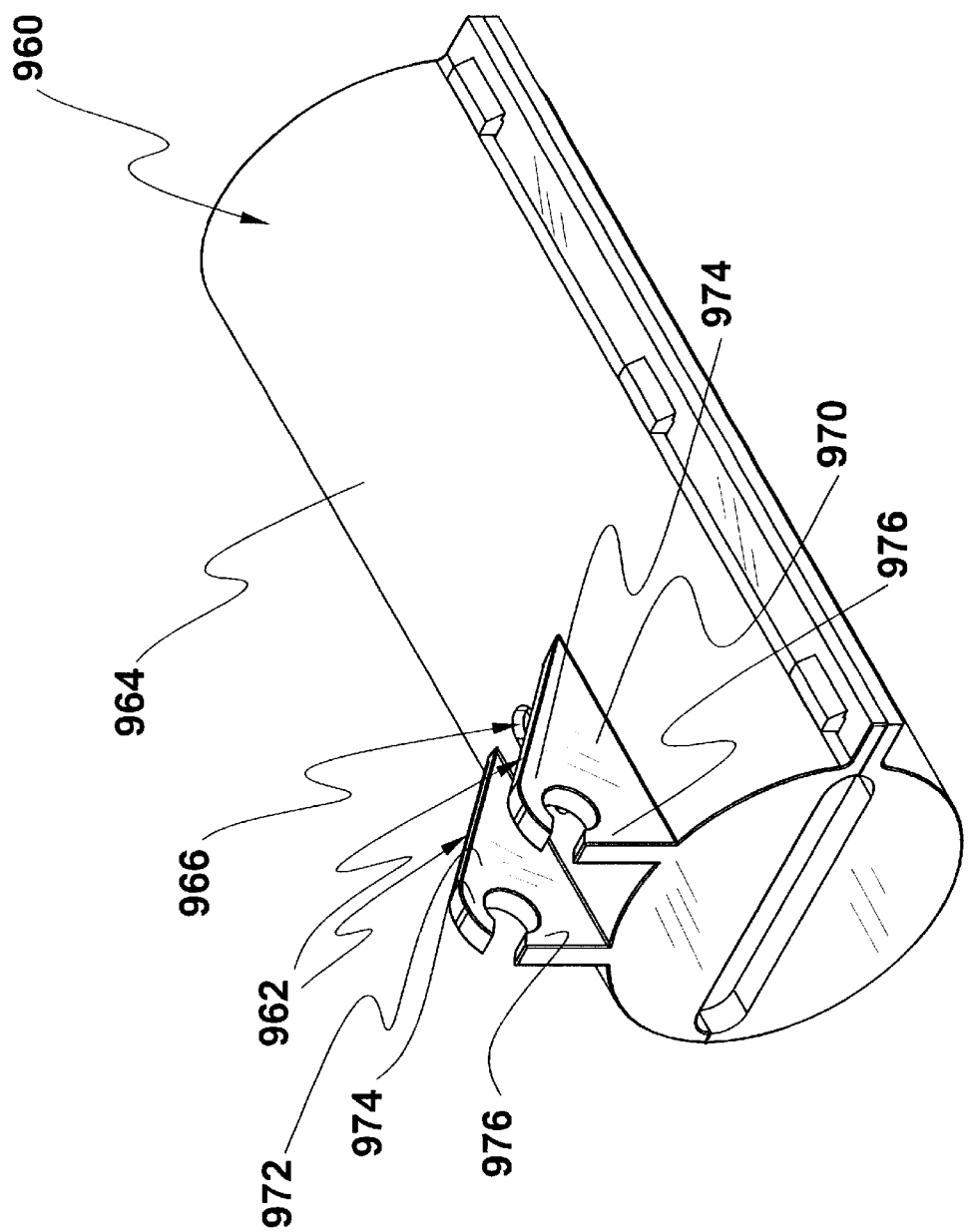
FIG. 35 is a perspective of the cord container of FIG. 34 closed for viewing an adapter affixed thereto.

FIGS. 34 and 35 depict a container 960 for an umbilical cord (not shown) from which blood samples are drawn. Container 960 has a connector 962 affixed to an outside surface 964 which is formed to provide needle tip 100 protected access through an orifice 966 to the umbilical cord. Connector 962 has a pair of outwardly jutting connecting members 970 and 972 which are similar in form and function to connecting members 908 and 910 (see FIG. 26). However, in the case of connector 962, connecting members have prongs 974 and 976 disposed to facilitate oblique entry through orifice 966 and into the umbilical cord. Container 960 is preferably injection molded from polypropylene, as is the case for adapters 902' and 902". The state of container 960 in FIG. 34 is the preferred "as molded configuration". As such, container 960 comprises a living hinge 980 connectively hinging two halves, 982 and 984, of container 960. Half 982 has a series of latches, each latch numbered 986, formed along an outside edge 988. Half 984 has a plurality of slots 990 along an outside edge 992 which juxtapose associated respective latches 986 and edge 988 when container 960 is closed about an umbilical cord for use. Each half 982 and 984 has at least one elongated indentation 994 which forms half of a cord clamp when container 960 is closed.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A medical needle safety system which can be used for repeatably accessing a medical needle from a needle tip protecting shield for in seriatim use of the needle, said safety system comprising:

a medical needle assembly comprising an elongated medical needle and a needle hub, said medical needle being securely affixed in the hub and having a distally disposed sharpened tip and a long axis which is medially disposed along a line from the hub to the tip;

a safety shield assembly hingeably associated with the hub and comprising a shield comprising a plurality of foldable segments each segment of which is hingeably affixed to at least one other segment, at least one of said segments being articulated to pivot about the long axis of the needle; and said shield assembly further comprising at least one releasable latching part which, when the shield is extended about the needle, latches to affix the shield for the purpose of providing a needle independent, substantially rigid structure protectively disposed about the needle and the needle tip and still further comprising an actuator by which the latch is released to permit the shield to be foldably retracted to bare the needle and needle tip for use and later reextended about the needle and its tip.

2. A medical needle safety system according to claim 1 wherein said shield assembly further comprises a needle guide and a hinge for affixing the guide to a distal segment of the shield to, thereby, permit the guide to rotate relative to the distal segment of the shield to linearly slide distally and proximally along the long axis of said needle as the shield is extended to cover the needle tip and foldably retracted to bare the needle and tip for use, respectively, said guide interacting with said needle to displace the needle tip into and out of the shield in such a manner that the needle tip is untouched by any part of the shield assembly.

3. A medical needle safety system according to claim 1 wherein said safety shield assembly comprises at least one distally disposed elongated part for communicating with said actuator to provide a releasing trigger on a distal end of said assembly.

4. A medical needle safety system according to claim 3 wherein a most distal segment of the shield comprises at least one member for connecting to a needle protecting connecting adapter which interfaces with needle pierceable targets to protect against inadvertent needle sticks, said member being juxtaposed a center of rotation of said needle guide such that no undue torque is placed upon the needle as said shield folds and unfolds while the needle is engaged with one of the pierceable targets.

5. A medical needle safety system according to claim 4 wherein said connecting member provides a guard against inadvertent displacement of said elongated trigger releasing part.

6. A medical needle safety system according to claim 4 wherein said connecting member comprises an elongated structure, comprising a longer dimension orthogonal to a shorter dimension, the longer dimension being substantially in line with the long axis of the needle when the shield is disposed to cover the needle and being angularly displaced by rotation of the shield about the needle as the needle is bared for use such that the longer dimension is substantially out-of-line with the long axis of the needle.

7. A medical needle safety system according to claim 4 further comprising the needle protecting adapter to which said at least one member interfaces.

8. A medical needle safety system according to claim 7 wherein said at least one member and needle protecting adapter, in combination, comprise a releasable interface.

9. A medical needle safety system according to claim 8 wherein said releasable interface comprises a connecting linkage which can only be selectively separated when the shield is extended.

10. A medical needle safety system according to claim 7 wherein said at least one member and needle protecting adapter together comprise elements of a lock and key combination which comprises a releasable interface in which one element of said combination acts as a lock and the other element acts as a key to assure integrity of the releasable latch against inadvertent release.

11. A medical needle safety system according to claim 7 wherein said adapter comprises a connection to a vacuum sampling tube.

12. A medical needle safety system according to claim 7 wherein said adapter comprises a connection to an umbilical cord sampling apparatus.

13. A medical needle safety system according to claim 7 wherein said adapter comprises a vial connecting element.

14. A medical needle safety system according to claim 7 wherein said adapter comprises a connector for attachment to a "Y" injection site.

15. A medical needle safety system according to claim 1 further comprising a syringe affixed to said needle hub.

16. A medical needle safety system according to claim 1 further comprising a locking part associated with the latching part, said locking part acting in combination with a catch disposed in said shield to deny further access to the needle and needle tip.

17. A combination for a safety medical needle system, said combination comprising:

a medical needle assembly comprising a medical needle with a sharpened tip and a hub in which said needle is securely affixed;

a linearly displaceable protective sheath securely, but releasibly latchable to a needle and needle tip protecting state when the medical needle system is not being used in a medical procedure and unlatchable and displaceable to bare the needle and needle tip for use in a subsequent medical procedure;

an actuator which communicates with the protective sheath for latching and unlatching the protective sheath; and an adapter which communicates with the actuator to unlatch and relatch the sheath and which provides an interface between a target fluid space, which is accessible through a needle piercing covering, and the medical needle assembly, said adapter further providing a protected passageway for the needle tip and a portion of the needle while the needle is displaced from the protective sheath.

18. A combination according to claim 17 wherein said protective sheath comprises a guide which acts to steer the needle as the sheath is displaced from the needle tip protecting state and as the sheath is returned to the protecting state such that the needle tip does not contact any portion of the protective sheath.

19. A combination according to claim 17 wherein said protective sheath and adapter comprise connective parts which, when joined, urge the protective sheath to retract from protectively shielding the needle and needle tip thereby delivering the needle tip through the protecting adapter to pierce the covering and which are releasable only when the protective sheath is extended to protect the needle and needle tip, thereby assuring continuous protection of the needle and needle tip when using the combination.

20. A combination according to claim 19 wherein said connective parts comprise a selectively disposed hinge which is articulated in a manner which retracts the sheath without placing undue transverse forces upon the needle.

21. A method for using a medical needle safety system which can be employed for repeatably accessing a medical needle from a needle tip protecting shield for in seriatim use of the needle, comprising the following steps:

(a) providing a medical needle assembly comprising an elongated medical needle and needle hub in which said medical needle is securely affixed, said medical needle having a distally disposed sharpened tip and a long axis which is medially disposed along a line from the hub to the tip;

(b) further providing a safety shield hingeably associated with the hub and comprising a plurality of foldable segments each of which is hingeably affixed to at least one other segment, at least one of such segments being articulated to pivot about the long axis of the needle, at least one releasable latch which affixes the shield relative to the needle to provide a substantially rigid apparatus independent of the needle and a secure safety cover for the needle tip when the shield is extended about the needle, an actuator by which the latch is released to permit the shield to be foldably retracted to bare the needle and needle tip for use;

(c) when the shield is extended, applying a force against the actuator to release the latch;

(d) folding the shield to bare the needle associated needle tip;

(e) using the needle in a portion of a predetermined procedure;

(f) extending the shield to provide a safety cover for the needle; and (g) repeating steps (d) through (f) until all portions of the predetermined procedure have been completed.

22. A method for using a medical needle safety system according to claim 21 further comprising the step of providing a needle guide, affixed to a distal segment of the shield, which is disposed to slide distally and proximally upon said needle as the shield is extended to cover the needle tip and foldably retracted to bare the needle and tip for use, respectively, said guide interacting with said needle to displace the needle tip into and out of the shield in such a manner that the tip is untouched by any part of the shield.

23. A method for using a medical needle safety system according to claim 22 adding to step (d) a step of guiding the needle tip from the distal section without causing the needle to touch the distal section as the needle and needle tip are displaced from protective cover of the shield.

24. A method for using a medical needle safety system according to claim 22 adding to step (f) a step of guiding the needle tip into protective cover of the distal section without allowing the needle to touch the distal section as the needle and needle tip are displaced to protective cover of the shield.

25. A method for using a medical needle safety system according to claim 21 wherein the safety shield providing step comprises providing a lock which securely and unreleasibly affixes the shield about the needle and needle tip.

26. A method for using a medical needle safety system according to claim 25 comprising the additional step of:

(h) engaging the lock.

27. A method for using a medical needle safety system according to claim 21 wherein the safety shield providing step comprises providing a connective interface affixed to the most distal segment of the shield, said connective interface being disposed at a center of rotation about and along the needle by the distal segment as the segment pivots while the shield folds and unfolds.

28. A method for using a medical needle safety system according to claim 27 further comprising a step for providing an adapter associated with a vessel having a portal accessible via a needle pierceable membrane, said adapter comprising a part which links to the connective interface and which communicates with the actuator to provide a distally disposed release of said releasable latch and further comprising a needle shielding pathway between said sheath and the pierceable membrane.

29. A method for using a medical needle safety system according to claim 28 wherein step (c) comprises applying the force against the actuator via the adapter.

30. A method for using a medical needle safety system according to claim 29 wherein step (d) comprises folding the sheath without placing undue transverse forces on the needle.

31. A method for using a medical needle safety system according to claim 30 wherein step (e) comprises using the needle to pierce the membrane.

32. A method for using a medical needle safety system according to claim 31 wherein step (f) comprises extending the shield by displacing the adapter distally to thereby provide a safety cover for the needle.

33. A method for using a medical needle safety system according to claim 28 wherein said adapter comprises an interface to one membrane target site selected from a group of such sites comprising drug vials, vacuum sampling tubes, umbilical cord containers, IV sets, hypodermic applications and blood vessels.

* * * * *